(12) United States Patent
Kikuchi et al.

(10) Patent No.: US 7,576,064 B2
(45) Date of Patent: Aug. 18, 2009

(54) PYRAZOLE DERIVATIVE, DRUG COMPOSITION CONTAINING THE SAME AND PRODUCTION INTERMEDIATE THEREFOR

(75) Inventors: Norihiko Kikuchi, Hotaka-machi (JP); Hideki Fujikura, Hotaka-machi (JP); Shigeki Tazawa, Hotaka-machi (JP); Tokuhisa Yamato, Tokyo (JP); Masayuki Isaji, Hotaka-machi (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 76 days.

(21) Appl. No.: 10/561,217

(22) PCT Filed: Jun. 15, 2004

(86) PCT No.: PCT/JP2004/008695

§ 371 (c)(1),
(2), (4) Date: Nov. 13, 2006

(87) PCT Pub. No.: WO2004/113359

PCT Pub. Date: Dec. 29, 2004

(65) Prior Publication Data

US 2007/0060531 A1    Mar. 15, 2007

(30) Foreign Application Priority Data

Jun. 20, 2003    (JP) ............................ 2003-175663

(51) Int. Cl.
 *A01N 43/04* (2006.01)
 *A61K 31/70* (2006.01)
 *C07H 17/00* (2006.01)
(52) U.S. Cl. .......................... 514/27; 514/25; 514/866; 536/4.1; 536/18.1
(58) Field of Classification Search ............... None
See application file for complete search history.

(56) References Cited

U.S. PATENT DOCUMENTS

| | | | |
|---|---|---|---|
| 4,526,895 A | 7/1985 | Jarreau et al. | |
| 2002/0052326 A1 | 5/2002 | Mathias et al. | |
| 2004/0006025 A1 | 1/2004 | Ohsumi et al. | |
| 2004/0063646 A1 | 4/2004 | Fujikura et al. | |
| 2004/0110936 A1 | 6/2004 | Ohsumi et al. | |
| 2004/0116357 A1 | 6/2004 | Fushimi et al. | |
| 2004/0176308 A1 | 9/2004 | Shiohara et al. | |

FOREIGN PATENT DOCUMENTS

| EP | 1568380 | * | 8/2005 |
|---|---|---|---|
| WO | WO 02/088157 A1 | | 11/2002 |
| WO | WO 02/098893 A1 | | 12/2002 |
| WO | WO2004/050122 | * | 6/2004 |

\* cited by examiner

*Primary Examiner*—Traviss C McIntosh, III
(74) *Attorney, Agent, or Firm*—Sughrue Mion, PLLC

(57) ABSTRACT

The present invention provides pyrazole derivatives represented by the general formula:

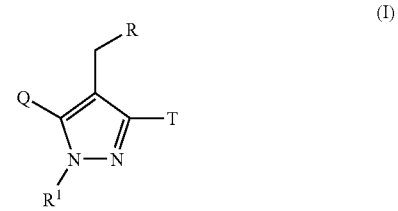

wherein $R^1$ represents H, an optionally substituted $C_{1-6}$ alkyl, etc.; one of Q and T represents a group selected from the following:

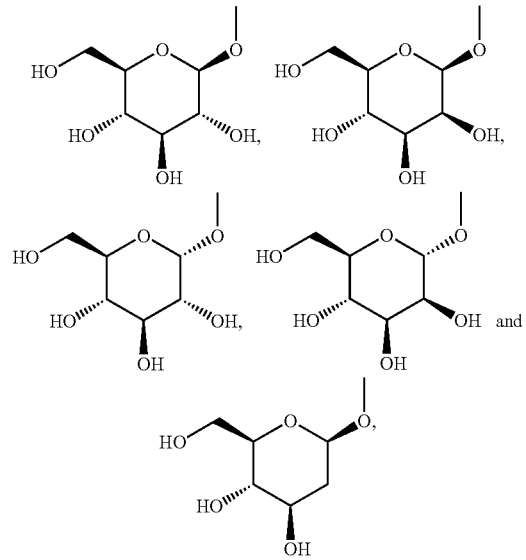

and the other represents -Z-Ar wherein Z represents —O—, —S—, etc.; Ar represents an optionally substituted $C_{6-10}$ aryl, etc.;
R represents an optionally substituted $C_{3-8}$ cycloalkyl, an optionally substituted $C_{6-10}$ aryl, etc., pharmaceutically acceptable salts thereof, and prodrugs thereof, which exhibit an excellent inhibitory activity in human sodium/glucose cotransporter (SGLT) and are useful as agents for the prevention, inhibition of progression or treatment of a disease associated with the excess uptake of at least a kind of carbohydrates selected from glucose, fructose and mannose (diabetes, postprandial hyperglycemia, impaired glucose tolerance, diabetic complications, etc.), and pharmaceutical compositions containing the same, medicinal uses thereof and intermediates for production therefor.

9 Claims, 1 Drawing Sheet

PYRAZOLE DERIVATIVE, DRUG COMPOSITION CONTAINING THE SAME AND PRODUCTION INTERMEDIATE THEREFOR

TECHNICAL FIELD

The present invention relates to pyrazole derivatives, pharmaceutically acceptable salts thereof or prodrugs thereof which are useful as medicaments, pharmaceutical compositions comprising the same and intermediates for production therefor.

More particularly, the present invention relates to pyrazole derivatives having an inhibitory activity to a sodium/glucose cotransporter, pharmaceutically acceptable salts thereof or prodrugs thereof which are useful as agents for the prevention, inhibition of progression or treatment of diseases associated with the excess uptake of at least a kind of carbohydrates selected from glucose, fructose and mannose such as diabetes, postprandial hyperglycemia, impaired glucose tolerance and diabetic complications, pharmaceutical compositions comprising the same and intermediates for production therefor.

BACKGROUND ART

Glucose, one of the most important energy sources for body, is taken up into a cell across cell membrane to be made available in the body. A membrane protein called glucose transporter is involved in this uptake at cell membrane. Glucose transporter is classified into two main categories of facilitated glucose transporter which uptakes glucose depending on intracellular and extracellular glucose concentration difference, and sodium/glucose cotransporter (SGLT) which uptakes glucose by using intracellular and extracellular ion concentration difference (for example, see Reference 1). Regarding SGLT, it has been known that SGLT1, sodium/glucose cotransporter having a high affinity, mainly exists in human small intestine, and SGLT2, sodium/glucose cotransporter having a low affinity, mainly exists in human renal tubule (for example, see References 2 and 3). It is reported that absorption of glucose and galactose is inadequate in patients with human SGLT1 dysfunction due to congenital abnormality, and that confirms SGLT1 participates in the absorption of glucose and galactose (see References 4 and 5). In addition, it has been confirmed that mRNA and protein of SGLT1 increase and the absorption of glucose or the like is accelerated in OLETF rat or streptozotocin-induced diabetic rats (for example, see References 6 and 7). In diabetic patients digestion and absorption of carbohydrates is generally accelerated, and it has been confirmed that, for example, hyperexpression of mRNA and protein of SGLT1 is found in human small intestine (for example, see Reference 8).

It is reported that SGLT2 is present in the segment S1 of renal proximal tubule and participates mainly in reabsorption of glucose filtrated through glomerulus (for example, see Reference 9).

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. Now, based on the background of rapid increase of diabetic patients, various agents have been developed, and biguanides, sulfonylureas, insulin sensitivity enhancers, α-glucosidase inhibitors and the like have been employed. However, biguanides and sulfonylureas show occasionally adverse effects such as lactic acidosis and hypoglycemia, respectively. Insulin sensitivity enhancers show occasionally adverse effects such as edema, and are concerned for advancing obesity. In addition, α-glucosidase inhibitors that delay digestion and absorption of carbohydrates at the small intestine are used for improvement of postprandial hyperglycemia. It is reported that acarbose, one of such agents, has an effect to prevent or delay diabetes onset when applied to a patient with impaired glucose tolerance (for example, see Reference 10). However, α-glucosidase inhibitors do not affect to increase of blood glucose level by digestion of glucose, monosaccharide (for example, see Reference 11), and an agent to have abroad inhibitory effect of the absorption of carbohydrates have been still desired based on the background of recent changes in constitution of carbohydrates in meals.

In addition, it has been known that blood mannose level increases in diabetes (for example, see Reference 12), and that blood mannose level has a positive correlation with blood glucose level and triglyceride level and a negative correlation with HDL cholesterol in metabolic syndrome (for example, see Reference 13). Mannose and fructose are known to accumulate in renal glomerulus in diabetic rats, and their relations with onset or progression of diabetic nephropathy have been pointed out (for example, see Reference 14). Moreover, it has been reported that mannose and fructose have a protein glycation ability more than 5-times as glucose in glycation reaction with proteins considered as a cause of diabetic complications (for example, see Reference 15). It is known that fructose consumes a lot of ATP through the intracellular metabolic pathway and forms lactose, and that causes a so-called fructose toxicity (for example, see the following Reference 16). Thus, diabetes causes various pathological conditions, and its exacerbation may have a risk to diabetic complications. In recent years, many large-scale clinical studies have been conducted for the prevention of onset or progression of diabetic complications in diabetic treatment, and they have provided many findings (for example, see References 17 and 18). Furthermore, many epidemiologic studies on impaired glucose tolerance and macroangiopathy show that impaired glucose tolerance as the boundary type is also a risk factor in macroangiopathy as well as diabetes. Thus, needs to improve postprandial hyperglycemia have been focused (for example, see Reference 19).

Under the above-mentioned circumstance, as SGLT inhibitors, SGLT1 inhibitors that inhibit the absorption of carbohydrates such as glucose at the small intestine by inhibiting human SGLT1 and inhibit the increase of blood glucose level and are useful specially for improvement of postprandial hyperglycemia and SGLT2 inhibitors, a novel type of antidiabetics, that increase the urinary glucose excretion and lower the blood glucose level by inhibiting excess reabsorption of glucose at the kidney have been found (for example, see References 20 to 28). Since a drug for promoting urinary glucose excretion makes excess glucose excrete into urine and that causes decrease of glucose accumulation in the body, effects to prevent or improve obesity and diuretic effects are expected. In addition, SGLT inhibitors are assumed to be useful for various diseases caused by hyperglycemia and associated with progression of diabetes or obesity. Moreover, as a result of a study using phlorizin known as a SGLT inhibitor, it was confirmed that by inhibiting SGLT urinary glucose excretion increased, blood glucose level lowered and insulin resistance was improved (for example, see References 29 and 30). Thus, in these years, various SGLT inhibitors has been found and are currently under development as treatment agents for diseases associated with glucose, lipid and energy metabolism including diabetes (for example, see References 31, 32 and 33).

In these years, a new gene that codes for a protein having a sodium/glucose cotransporting (hereinafter referred to as SMINT) activity was reported (see Reference 34) as a member of SGLT family. The DNA sequence (see Sequence number 1) and amino-acid sequence (see Sequence number 2) share high sequence homology with SGLT1 and SGLT2 and mammalian cells being expressed these genes show an activity of the sodium-dependent sugar uptake. As mentioned below, SMINT exists highly in human kidney and small intestine and has been confirmed to have a character transporting 1,5-anhydroglucitol, fructose and mannose in addition to glucose, and it has been found that SMINT has a function as 1,5-anhydroglucitol/fructose/mannose transporter. In addition, it was reported that 1,5-anhydroglucitol/fructose/mannose transporter functionally exists in the kidney or the like (for example, see References 35 and 36). Therefore, a SMINT inhibitor is considered to exert an inhibitory effect on 1,5-anhydroglucitol/fructose/mannose transporter and to be useful for the prevention, inhibition of progression or treatment of various diseases caused by excess uptake of glucose, fructose and mannose including diabetic complications such as diabetic nephropathy or the like.

As mentioned above, SGLT inhibitors such as SGLT1 inhibitors, SGLT2 inhibitors, SMINT inhibitors or the like are excellent agents useful for the prevention, inhibition of progression or treatment of various diseases including diabetes and diabetic complications. The present invention provides a novel compound that has an inhibitory effect on SGLT, inhibits the excess uptake of glucose, fructose, mannose and the like (in particular, the absorption in the small intestine or the reabsorption and the uptake into cells in the kidney) and is useful for the prevention, inhibition of progression or treatment of various diseases caused by excess uptake of at least a kind of carbohydrates selected from glucose, fructose and mannose.

Reference 1: Graeme I. Bell and 7 persons, Diabetes Care, March 1990, Vol.13, No.3, pp.198-208;

Reference 2: Matthias A. Hediger and 2 persons, Proc. Natl. Acad. Sci. USA, August 1989, Vol.86, pp.5748-5752;

Reference 3: Rebecca G. Wells and 5 persons, Am. J. Physiol., September 1992, Vol.263, pp.F459-465;

Reference 4: E. Turk and 4 persons, Nature, March 1991, Vol.350, pp.354-356;

Reference 5: Michihiro Kasahara and 2 persons, Saishin-igaku, January 1996, Vol.51, No.1, pp.84-90;

Reference 6: Y. Fujita and 5 persons, Diabetologia, 1998, Vol.41, pp.1459-1466;

Reference 7: J. Dyer and 5 persons, Biochem. Soc. Trans., 1997, Vol.25, p.479S;

Reference 8: J. Dyer and 4 persons, Am. J. Physiol., February 2002, Vol.282, No.2, pp.G241-G248;

Reference 9: Yoshikatsu Kanai and 4 persons, J. Clin. Invest., January 1994, Vol.93, pp.397-404;

Reference 10: Jean-Louis Chiasson and 5 persons, Lancet, June 2002, Vol.359, No.9323, pp.2072-2077;

Reference 11: Hiroyuki Odaka and 3 persons, Nihon Eiyo Syokuryo Gakkai Zasshi, 1992, Vol.45, p.27;

Reference 12: Elja Pitkänen, Clin. Chim. Acta, July 1996, Vol.251, No.1, pp.91-103;

Reference 13: O. M. Pitkänen and 2 persons, Scand J. Clin. Lab. Invest., December 1999, Vol.59, No.8, pp.607-612;

Reference 14: Li Ning Wang and 3 persons, Nippon Jinzo Gakkai Shi, 1990, Vol.32, No.4, pp.401-408;

Reference 15: H. Franklin Bunn and 1 person, Science, July 1981, Vol.213, pp.222-224;

Reference 16: R. Gitzelmann and 2 persons, The Metabolic and Molecular Bases of Inherited Disease, McGraw-Hill in the US, 1995, pp.905-934;

Reference 17: The Diabetes Control and Complications Trial Research Group, N. Engl. J. Med., September 1993, Vol.329, No.14, pp.977-986;

Reference 18: UK Prospective Diabetes Study Group, Lancet, September 1998, Vol.352, No.9131, pp.837-853;

Reference 19: Makoto Tominaga, Naibunpi-Tonyobyo-ka (Endocrine and Diabetes Clinic), November 2001, Vol.13, No.5, pp.534-542;

Reference 20: International Publication no.WO02/098893;

Reference 21: International Publication no.WO01/16147;

Reference 22: International Publication no.WO02/053573;

Reference 23: International Publication no.WO02/068439;

Reference 24: International Publication no.WO02/068440;

Reference 25: International Publication no.WO02/36602;

Reference 26: International Publication no.WO02/088157;

Reference 27: International Publication no.WO03/020737;

Reference 28: Japan Patent Publication no.JP2003-12686;

Reference 29: Luciano Rossetti and 4 persons, J. Clin. Invest., May 1987, Vol.79, pp.1510-1515;

Reference 30: Barbara B. Kahn and 4 persons, J. Clin. Invest., February 1991, Vol.87, pp.561-570;

Reference 31: Kenji Arakawa and 7 persons, Br. J. Pharmacol., January 2001, Vol.132, No.2, pp.578-586;

Reference 32: Masayuki Isaji and 8 persons, FASEB J., March 2001, Vol.15, No.4, p.A214;

Reference 33: Kenji Katsuno and 7 persons, FASEB J., March 2001, Vol.15, No.4, p.A214;

Reference 34: Japan Patent Publication no.JP2004-000177;

Reference 35: Toshikazu Yamanouchi and 5 persons, Biochim. Biophys. Acta., August 1996, Vol.1291, No.1, pp.89-95;

Reference 36: T. Blasco and 5 persons, J. Membr. Biol., November 2000, Vol.178, No.2, pp.127-135.

DISCLOSURE OF THE INVENTION

The present inventors have studied earnestly to find SGLT inhibitors. As a result, it was found that pyrazole derivatives represented by the following general formula (I) show an inhibitory activity in SGLT1, SGLT2 and/or SMINT and are excellent drugs inhibiting excess uptake of at least a kind of carbohydrates selected from glucose, fructose and mannose as shown below, thereby forming the basis of the present invention.

That is, the present invention relates to

[1] a pyrazole derivative represented by the following general formula:

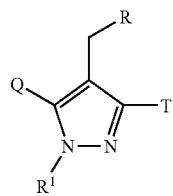

(I)

wherein $R^1$ represents a hydrogen atom, a $C_{1-6}$ alkyl group which may have the same or different 1 to 3 groups selected from the following substituent group (A), a $C_{2-6}$ alkenyl group which may have the same or different 1 to 3 groups selected from the following substituent group (A), a $C_{2-6}$ alkynyl group which may have the same or different 1 to 3 groups selected from the following substituent group (A), a $C_{3-8}$ cycloalkyl group which may have the same or different 1 to 3 groups selected from the following substituent group (A), a $C_{6-10}$ aryl group which may have the same or different 1 to 3 groups selected from the following substituent group (B), a $C_{2-9}$ heterocycloalkyl group which may have the same or different 1 to 3 groups selected from the following substituent group (A), or a $C_{1-9}$ heteroaryl group which may have the same or different 1 to 3 groups selected from the following substituent group (B);

one of Q and T represents a group selected from

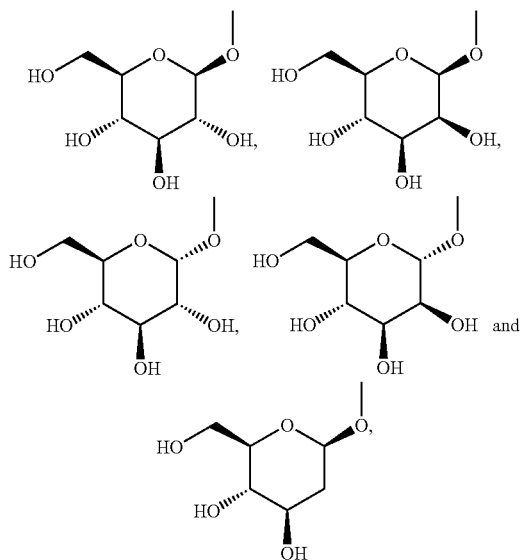

and the other represents a group represented by the formula: -Z-Ar wherein Ar represents a $C_{6-10}$ aryl group which may have the same or different 1 to 3 groups selected from the following substituent group (B) or a $C_{1-9}$ heteroaryl group which may have the same or different 1 to 3 groups selected from the following substituent group (B); and Z represents —O—, —S— or —NY— (in which Y represents a hydrogen atom or a $C_{1-6}$ alkyl group), an aliphatic cyclic amino group which may have the same or different 1 to 3 groups selected from the following substituent group (A), or an aromatic cyclic amino group which may have the same or different 1 to 3 groups selected from the following substituent group (B);

R represents a $C_{3-8}$ cycloalkyl group which may have the same or different 1 to 3 groups selected from the following substituent group (A), a $C_{6-10}$ aryl group which may have the same or different 1 to 3 groups selected from the following substituent group (B), a $C_{2-9}$ heterocycloalkyl group which may have the same or different 1 to 3 groups selected from the following substituent group (A), or a $C_{1-9}$ heteroaryl group which may have the same or different 1 to 3 groups selected from the following substituent group (B);

[substituent group (A)]:

a halogen atom, a nitro group, a cyano group, an oxo group, -$G^1$, —$OG^2$, —$SG^2$, —$N(G^2)_2$, —$C(=O)G^2$, —$C(=O)OG^2$, —$C(=O)N(G^2)_2$, —$S(=O)_2G^2$, —$S(=O)_2OG^2$, —$S(=O)_2N(G^2)_2$, —$S(=O)G^1$, —$OC(=O)G^1$, —$OC(=O)N(G^2)_2$, —$NHC(=O)G^2$, —$OS(=O)_2G^1$, —$NHS(=O)_2G^1$ and —$C(=O)NHS(=O)_2G^1$;

[substituent group (B)]:

a halogen atom, a nitro group, a cyano group, -$G^1$, —$OG^2$, —$SG^2$, —$N(G^2)_2$, -$G^3OG^4$, -$G^3N(G^4)_2$, —$C(=O)G^2$, —$C(=O)OG^2$, —$C(=O)N(G^2)_2$, —$S(=O)_2G^2$, —$S(=O)_2OG^2$, —$S(=O)_2N(G^2)_2$, —$S(=O)G^1$, —$OC(=O)G^1$, —$OC(=O)N(G^2)_2$, —$NHC(=O)G^2$, —$OS(=O)_2G^1$, —$NHS(=O)_2G^1$ and —$C(=O)NHS(=O)_2G^1$;

in the above substituent group (A) and/or (B), $G^1$ represents a $C_{1-6}$ alkyl group which may have the same or different 1 to 3 groups selected from the following substituent group (C), a $C_{2-6}$ alkenyl group which may have the same or different 1 to 3 groups selected from the following substituent group (C), a $C_{2-6}$ alkynyl group which may have the same or different 1 to 3 groups selected from the following substituent group (C), a $C_{3-8}$ cycloalkyl group which may have the same or different 1 to 3 groups selected from the following substituent group (C), a $C_{6-10}$ aryl group which may have the same or different 1 to 3 groups selected from the following substituent group (D), a $C_{2-9}$ heterocycloalkyl group which may have the same or different 1 to 3 groups selected from the following substituent group (C), or a $C_{1-9}$ heteroaryl group which may have the same or different 1 to 3 groups selected from the following substituent group (D);

$G^2$ represents a hydrogen atom, a $C_{1-6}$ alkyl group which may have the same or different 1 to 3 groups selected from the following substituent group (C), a $C_{2-6}$ alkenyl group which may have the same or different 1 to 3 groups selected from the following substituent group (C), a $C_{2-6}$ alkynyl group which may have the same or different 1 to 3 groups selected from the following substituent group (C), a $C_{3-8}$ cycloalkyl group which may have the same or different 1 to 3 groups selected from the following substituent group (C), a $C_{6-10}$ aryl group which may have the same or different 1 to 3 groups selected from the following substituent group (D), a $C_{2-9}$ heterocycloalkyl group which may have the same or different 1 to 3 groups selected from the following substituent group (C), or a $C_{1-9}$ heteroaryl group which may have the same or different 1 to 3 groups selected from the following substituent group (D), and with the proviso that $G^2$ may be the same or different when there are 2 or more $G^2$ in the substituents;

$G^3$ represents a $C_{1-6}$ alkyl group;

$G^4$ represents a $C_{1-6}$ alkyl group which may have the same or different 1 to 3 groups selected from the following substituent group (C), and with the proviso that $G^4$ may be the same or different when there are 2 or more $G^4$ in the substituents;

[substituent group (C)]:

a halogen atom, a nitro group, a cyano group, an oxo group, -G$^5$, —OG$^6$, —SG$^6$, —N(G$^6$)$_2$, —C(=O)G$^6$, —C(=O)OG$^6$, —C(=O)N(G$^6$)$_2$, —S(=O)$_2$G$^6$, —S(=O)$_2$OG$^6$, —S(=O)$_2$N(G$^6$)$_2$, —S(=O)G$^5$, —OC(=O)G$^5$, —OC(=O)N(G$^6$)$_2$, —NHC(=O)G$^6$, —OS(=O)$_2$G$^5$, —NHS(=O)$_2$G$^5$ and —C(=O)NHS(=O)$_2$G$^5$; and

[substituent group (D)]:

a halogen atom, a nitro group, a cyano group, -G$^5$, —OG$^6$, —SG$^6$, —N(G$^6$)$_2$, —C(=O)G$^6$, —C(=O)OG$^6$, —C(=O)N(G$^6$)$_2$, —S(=O)$_2$G$^6$, —S(=O)$_2$OG$^6$, —S(=O)$_2$N(G$^6$)$_2$, —S(=O)G$^5$, —OC(=O)G$^5$, —OC(=O)N(G$^6$)$_2$, —NHC(=O)G$^6$, —OS(=O)$_2$G$^5$, —NHS(=O)$_2$G$^5$ and —C(=O)NHS(=O)$_2$G$^5$;

in the substituent group (C) and/or (D),

G$^5$ represents a C$_{1-6}$ alkyl group, a C$_{2-6}$ alkenyl group, a C$_{2-6}$ alkynyl, a C$_{3-8}$ cycloalkyl group, a C$_{6-10}$ aryl group, a C$_{2-9}$ heterocycloalkyl group or a C$_{1-9}$ heteroaryl group; and G$^6$ represents a hydrogen atom, a C$_{1-6}$ alkyl group, a C$_{2-6}$ alkenyl group, a C$_{2-6}$ alkynyl, a C$_{3-8}$ cycloalkyl group, a C$_{6-10}$ aryl group, a C$_{2-9}$ heterocycloalkyl group or a C$_{1-9}$ heteroaryl group, and with the proviso that G$^6$ may be the same or different when there are 2 or more G$^6$ in the substituents, or a pharmaceutically acceptable salt thereof or a prodrug thereof;

[2] a pyrazole derivative as described in the above [1], wherein Q represents a group represented by the formula: -Z-Ar$^1$ wherein Ar$^1$ represents a C$_{6-10}$ aryl group which may have the same or different 1 to 3 groups selected from the following substituent group (B); and Z represents —O—, —S— or —NY— (in which Y represents a hydrogen atom or a C$_{1-6}$ alkyl group), an aliphatic cyclic amino group which may have the same or different 1 to 3 groups selected from the following substituent group (A), or an aromatic cyclic amino group which may have the same or different 1 to 3 groups selected from the following substituent group (B); T represents a group selected from

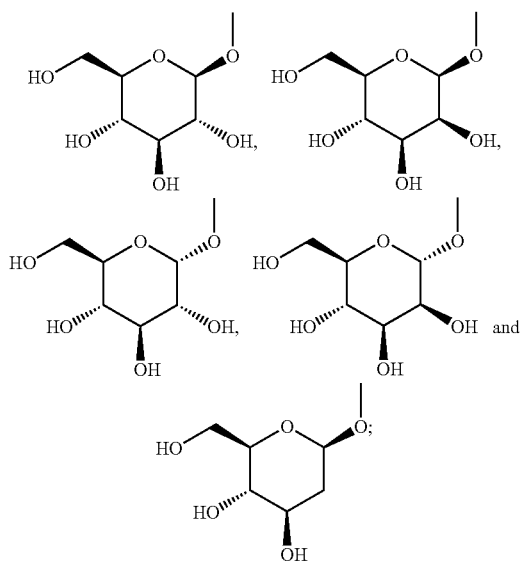

R represents a C$_{6-10}$ aryl group which may have the same or different 1 to 3 groups selected from the following substituent group (B);

[substituent group (B)]:

a halogen atom, a nitro group, a cyano group, -G$^1$, —OG$^2$, —SG$^2$, —N(G$^2$)$_2$, -G$^3$OG$^4$, -G$^3$N(G$^4$)$_2$, —C(=O)G$^2$, —C(=O)OG$^2$, —C(=O)N(G$^2$)$_2$, —S(=O)$_2$G$^2$, —S(=O)$_2$OG$^2$, —S(=O)$_2$N(G$^2$)$_2$, —S(=O)G$^1$, —OC(=O)G$^1$, —OC(=O)N(G$^2$)$_2$, —NHC(=O)G$^2$, —OS(=O)$_2$G$^1$, —NHS(=O)$_2$G$^1$ and —C(=O)NHS(=O)$_2$G$^1$;

in the above substituent group (B),

G$^1$ represents a C$_{1-6}$ alkyl group which may have the same or different 1 to 3 groups selected from the following substituent group (C), a C$_{2-6}$ alkenyl group which may have the same or different 1 to 3 groups selected from the following substituent group (C), a C$_{2-6}$ alkynyl group which may have the same or different 1 to 3 groups selected from the following substituent group (C), a C$_{3-8}$ cycloalkyl group which may have the same or different 1 to 3 groups selected from the following substituent group (C), a C$_{6-10}$ aryl group which may have the same or different 1 to 3 groups selected from the following substituent group (D), a C$_{2-9}$ heterocycloalkyl group which may have the same or different 1 to 3 groups selected from the following substituent group (C), or a C$_{1-9}$ heteroaryl group which may have the same or different 1 to 3 groups selected from the following substituent group (D);

G$^2$ represents a hydrogen atom, a C$_{1-6}$ alkyl group which may have the same or different 1 to 3 groups selected from the following substituent group (C), a C$_{2-6}$ alkenyl group which may have the same or different 1 to 3 groups selected from the following substituent group (C), a C$_{2-6}$ alkynyl group which may have the same or different 1 to 3 groups selected from the following substituent group (C), a C$_{3-8}$ cycloalkyl group which may have the same or different 1 to 3 groups selected from the following substituent group (C), a C$_{6-10}$ aryl group which may have the same or different 1 to 3 groups selected from the following substituent group (D), a C$_{2-9}$ heterocycloalkyl group which may have the same or different 1 to 3 groups selected from the following substituent group (C), or a C$_{1-9}$ heteroaryl group which may have the same or different 1 to 3 groups selected from the following substituent group (D), and with the proviso that G$^2$ may be the same or different when there are 2 or more G$^2$ in the substituents;

G$^3$ represents a C$_{1-6}$ alkyl group;

G$^4$ represents a C$_{1-6}$ alkyl group which may have the same or different 1 to 3 groups selected from the following substituent group (C), and with the proviso that G$^4$ may be the same or different when there are 2 or more G$^4$ in the substituents;

[substituent group (C)]:

a halogen atom, a nitro group, a cyano group, an oxo group, -G$^5$, —OG$^6$, —SG$^6$, —N(G$^6$)$_2$, —C(=O)G$^6$, —C(=O)OG$^6$, —C(=O)N(G$^6$)$_2$, —S(=O)$_2$G$^6$, —S(=O)$_2$OG$^6$, —S(=O)$_2$N(G$^6$)$_2$, —S(=O)G$^5$, —OC(=O)G$^5$, —OC(=O)N(G$^6$)$_2$, —NHC(=O)G$^6$, —OS(=O)$_2$G$^5$, —NHS(=O)$_2$G$^5$ and —C(=O)NHS(=O)$_2$G$^5$; and

[substituent group (D)]:

a halogen atom, a nitro group, a cyano group, -G$^5$, —OG$^6$, —SG$^6$, —N(G$^6$)$_2$—C(=O)G$^6$, —C(=O)OG$^6$, —C(=O)N(G$^6$)$_2$, —S(=O)$_2$G$^6$, —S(=O)$_2$OG$^6$, —S(=O)$_2$N(G$^6$)$_2$, —S(=O)G$^5$, —OC(=O)G$^5$, —OC(=O)N(G$^6$)$_2$, —NHC(=O)G$^6$, —OS(=O)$_2$G$^5$, —NHS(=O)$_2$G$^5$ and —C(=O)NHS(=O)$_2$G$^5$;

in the substituent group (C) and/or (D),

G$^5$ represents a C$_{1-6}$ alkyl group, a C$_{2-6}$ alkenyl group, a C$_{2-6}$ alkynyl, a C$_{3-8}$ cycloalkyl group, a C$_{6-10}$ aryl group, a C$_{2-9}$ heterocycloalkyl group or a C$_{1-9}$ heteroaryl group; and $G^6$ represents a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group, and with the proviso that $G^6$ may be the same or different when there are 2 or more $G^6$ in the substituents, or a pharmaceutically acceptable salt thereof or a prodrug thereof;

[3] a pharmaceutical composition comprising as an active ingredient a pyrazole derivative as described in the above [1] or [2], or a pharmaceutically acceptable salt thereof or a prodrug thereof;

[4] a pharmaceutical composition as described in the above [3] wherein the composition is a sodium/glucose cotransporter inhibitor;

[5] a pharmaceutical composition as described in the above [3] or [4] wherein a target disease is a disease caused by excess uptake of at least a kind of carbohydrate selected from glucose, fructose and mannose;

[6] a pharmaceutical composition as described in the above [5] wherein the target disease is selected from a group consisting of diabetes, postprandial hyperglycemia, impaired glucose tolerance, diabetic complications, obesity, hyperinsulinemia, hyperlipidemia, hypercholesterolemia, hypertriglyceridemia, lipid metabolism disorders, atherosclerosis, hypertension, congestive heart failure, edematous state, metabolic acidosis, syndrome X, hyperuricemia, gout and nephritis;

[7] a pharmaceutical composition as described in any one of the above [3]-[6], which comprises at least one drug selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, a hydroxymethylglutaryl coenzyme A reductase inhibitor, a fibric acid derivative, a $β_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an anti-platelets agent, a uric acid synthesis inhibitor, a uricosuric agent and a urinary alkalinizer;

[8] a pyrazole derivative represented by the general formula:

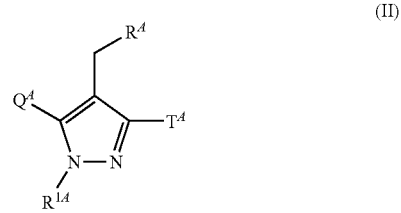

(II)

wherein $R^{1A}$ represents a hydrogen atom, a $C_{1-6}$ alkyl group which may have the same or different 1 to 3 groups selected from the following substituent group (A1), a $C_{2-6}$ alkenyl group which may have the same or different 1 to 3 groups selected from the following substituent group (A1), a $C_{2-6}$ alkynyl group which may have the same or different 1 to 3 groups selected from the following substituent group (A1), a $C_{3-8}$ cycloalkyl group which may have the same or different 1 to 3 groups selected from the following substituent group (A1), a $C_{6-10}$ aryl group which may have the same or different 1 to 3 groups selected from the following substituent group (B1), a $C_{2-9}$ heterocycloalkyl group which may have the same or different 1 to 3 groups selected from the following substituent group (A1), or a $C_{1-9}$ heteroaryl group which may have the same or different 1 to 3 groups selected from the following substituent group (B1);

one of $Q^A$ and $T^A$ represents a group selected from

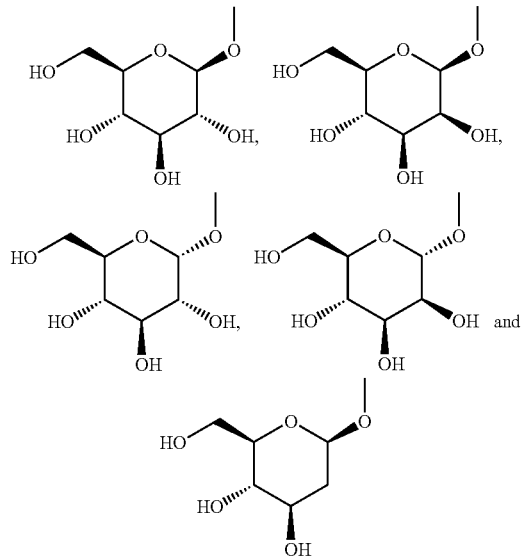

which has a protective group, and the other represents a group represented by the formula: $-Z^A Ar^A$ wherein $Ar^A$ represents a $C_{6-10}$ aryl group which may have the same or different 1 to 3 groups selected from the following substituent group (B1) or a $C_{1-9}$ heteroaryl group which may have the same or different 1 to 3 groups selected from the following substituent group (B1); and $Z^A$ represents —O—, —S— or —$NY^A$— (in which $Y^A$ represents a hydrogen atom, a $C_{1-6}$ alkyl group or a protective group), an aliphatic cyclic amino group which may have the same or different 1 to 3 groups selected from the following substituent group (A1), or an aromatic cyclic amino group which may have the same or different 1 to 3 groups selected from the following substituent group (B1);

$R^A$ represents a $C_{3-8}$ cycloalkyl group which may have the same or different 1 to 3 groups selected from the following substituent group (A1), a $C_{6-10}$ aryl group which may have the same or different 1 to 3 groups selected from the following substituent group (B1), a $C_{2-9}$ heterocycloalkyl group which may have the same or different 1 to 3 groups selected from the following substituent group (A1), or a $C_{1-9}$ heteroaryl group which may have the same or different 1 to 3 groups selected from the following substituent group (B1);

[substituent group (A1)]:

a halogen atom, a nitro group, a cyano group, an oxo group, $-G^{1A}$, $-OG^{2B}$, $-SG^{2B}$, $-N(G^{2B})_2$, $-C(=O)G^{2A}$, $-C(=O)OG^{2B}$, $-C(=O)N(G^{2B})_2$, $-S(=O)_2G^{2A}$, $-S(=O)_2OG^{2A}$, $-S(=O)_2N(G^{2B})_2$, $-S(=O)G^{1A}$, $-OC(=O)G^{1A}$, $-OC(=O)N(G^{2B})_2$, $-NHC(=O)G^{2A}$, $-OS(=O)_2G^{1A}$, $-NHS(=O)_2G^{1A}$, and $-C(=O)NHS(=O)_2G^{1A}$;

[substituent group (B1)]:

a halogen atom, a nitro group, a cyano group, $-G^{1A}$, $-OG^{2B}$, $-SG^{2B}$, $-N(G^{2B})_2$, $-G^3OG^{4B}$, $-G^3N(G^{4A})_2$, $-C(=O)G^{2A}$, $-C(=O)OG^{2B}$, $-C(=O)N(G^{2B})_2$, $S(=O)_2G^{2A}$, $-S(=O)_2OG^{2A}$, $-S(=O)_2N(G^{2B})_2$, $-S(=O)G^{1A}$, $-OC(=O)G^{1A}$, $-OC(=O)N(G^{2B})_2$, $-NHC(=O)G^{2A}$, $-OS(=O)_2G^{1A}$, $NHS(=O)_2G^{1A}$ and $-C(=O)NHS(=O)_2G^{1A}$;

in the above substituent group (A1) and/or (B1), $G^{1A}$ represents a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1);

$G^{2A}$ represents a hydrogen atom, a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1);

$G^{2B}$ represents a protective group, a hydrogen atom, a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1); and with the proviso that $G^{2B}$ may be the same or different when there are 2 or more $G^{2B}$ in the substituents;

$G^3$ represents a $C_{1-6}$ alkyl group;

$G^{4A}$ represents a $C_{1-6}$ alkyl group which may have the same or different 1 to 3 groups selected from the following substituent group (C1), and with the proviso that $G^{4A}$ may be the same or different when there are 2 or more $G^{4A}$ in the substituents;

[substituent group (C1)]:

a halogen atom, a nitro group, a cyano group, an oxo group, $-G^5$, $-OG^{6A}$, $-SG^{6A}$, $-N(G^{6A})_2$, $-C(=O)G^6$, $-C(=O)OG^{6A}$, $-C(=O)N(G^{6A})_2$, $-S(=O)_2G^6$, $-S(=O)_2OG^6$, $-S(=O)_2N(G^{6A})_2$, $-S(=O)G^5$, $-OC(=O)G^5$, $-OC(=O)N(G^{6A})_2$, $-NHC(=O)G^6$, $-OS(=O)_2G^5$, $-NHS(=O)_2G^5$ and $-C(=O)NHS(=O)_2G^5$; and

[substituent group (D1)]:

a halogen atom, a nitro group, a cyano group, $-G^5$, $-OG^{6A}$, $-SG^{6A}$, $N(G^{6A})_2$, $-C(=O)G^6$, $-C(=O)OG^{6A}$, $-C(=O)N(G^{6A})_2$, $-S(=O)_2G^6$, $-S(=O)_2OG^6$, $-S(=O)_2N(G^{6A})_2$, $-S(=O)G^5$, $-OC(=O)G^5$, $-OC(=O)N(G^{6A})_2$, $-NHC(=O)G^6$, $-OS(=O)_2G^5$, $-NHS(=O)_2G^5$ and $-C(=O)NHS(=O)_2G^5$;

in the substituent group (C1) and/or (D1), $G^5$ represents a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group; and $G^6$ represents a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group;

$G^{6A}$ represents a protective group, a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group, and with the proviso that $G^{6A}$ may be the same or different when there are 2 or more $G^{6A}$ in the substituents, or a pharmaceutically acceptable salt thereof;

[9] a pyrazole derivative represented by the general formula:

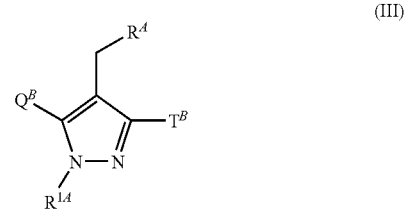

(III)

wherein $R^{1A}$ represents a hydrogen atom, a $C_{1-6}$ alkyl group which may have the same or different 1 to 3 groups selected from the following substituent group (A1), a $C_{2-6}$ alkenyl group which may have the same or different 1 to 3 groups selected from the following substituent group (A1), a $C_{2-6}$ alkynyl group which may have the same or different 1 to 3 groups selected from the following substituent group (A1), a $C_{3-8}$ cycloalkyl group which may have the same or different 1 to 3 groups selected from the following substituent group (A1), a $C_{6-10}$ aryl group which may have the same or different 1 to 3 groups selected from the following substituent group (B1), a $C_{2-9}$ heterocycloalkyl group which may have the same or different 1 to 3 groups selected from the following substituent group (A1), or a $C_{1-9}$ heteroaryl group which may have the same or different 1 to 3 groups selected from the following substituent group (B1);

one of $Q^B$ and $T^B$ represents a hydroxy group, and the other represents a group represented by the formula: $-Z^A-Ar^A$ wherein $Ar^A$ represents a $C_{6-10}$ aryl group which may have the same or different 1 to 3 groups selected from the following substituent group (B1) or a $C_{1-9}$ heteroaryl group which may have the same or different 1 to 3 groups selected from the following substituent group (B1); and $Z^A$ represents —O—, —S— or —$NY^A$— (in which $Y^A$ represents a hydrogen atom, a $C_{1-6}$ alkyl group or a protective group), an aliphatic cyclic amino group which may have the same or different 1 to 3 groups selected from the following substituent group (A1), or an aromatic cyclic amino group which may have the same or different 1 to 3 groups selected from the following substituent group (B1);

$R^A$ represents a $C_{3-8}$ cycloalkyl group which may have the same or different 1 to 3 groups selected from the following substituent group (A1), a $C_{6-10}$ aryl group which may have the same or different 1 to 3 groups selected from the following substituent group (B1), a $C_{2-9}$ heterocycloalkyl group which may have the same or different 1 to 3 groups selected from the following substituent group (A1), or a $C_{1-9}$ heteroaryl group which may have the same or different 1 to 3 groups selected from the following substituent group (B1);

[substituent group (A1)]:

a halogen atom, a nitro group, a cyano group, an oxo group, $-G^{1A}$, $-OG^{2B}$, $-SG^{2B}$, $-N(G^{2B})_2$, $-C(=O)G^{2A}$, $-C(=O)OG^{2B}$, $-C(=O)N(G^{2B})_2$, $-S(=O)_2G^{2A}$, $-S(=O)_2OG^{2A}$, $-S(=O)_2N(G^{2B})_2$, $-S(=O)G^{1A}$, $-OC(=O)G^{1A}$, $-OC(=O)N(G^{2B})_2$, $-NHC(=O)G^{2A}$, $-OS(=O)_2G^{1A}$, $-NHS(=O)_2G^{1A}$ and $-C(=O)NHS(=O)_2G^{1A}$;

[substituent group (B1)]:

a halogen atom, a nitro group, a cyano group, $-G^{1A}$, $-OG^{2B}$, $-SG^{2B}$, $-N(G^{2B})_2$, $-G^3G^{4A}$, $-G^3N(G^{4A})_2$, $-C(=O)G^{2A}$, $-C(=O)OG^{2B}$, $-C(=O)N(G^{2B})_2$, $-S(=O)_2G^{2A}$, $-S(=O)_2OG^{2A}$, $-S(=O)_2N(G^{2B})_2$, $-S(=O)G^{1A}$, $-OC(=O)G^{1A}$, $-OC(=O)N(G^{2B})_2$, $-NHC(=O)G^{2A}$, $-OS(=O)_2G^{1A}$, $-NHS(=O)_2G^{1A}$ and $-C(=O)NHS(=O)_2G^{1A}$;

in the above substituent group (A1) and/or (B1), $G^{1A}$ represents a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1);

$G^{2A}$ represents a hydrogen atom, a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1);

$G^{2B}$ represents a protective group, a hydrogen atom, a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1); and with the proviso that $G^{2B}$ may be the same or different when there are 2 or more $G^{2B}$ in the substituents;

$G^3$ represents a $C_{1-6}$ alkyl group;

$G^{4A}$ represents a $C_{1-6}$ alkyl group which may have the same or different 1 to 3 groups selected from the following substituent group (C1), and with the proviso that $G^{4A}$ may be the same or different when there are 2 or more $G^{4A}$ in the substituents;

[substituent group (C1)]:

a halogen atom, a nitro group, a cyano group, an oxo group, $-G^5$, $OG^{6A}$, $-SG^{6A}$, $-N(G^{6A})_2$, $-C(=O)G^6$, $-C(=O)OG^{6A}$, $-C(=O)N(G^{6A})_2$, $-S(=O)_2G^6$, $-S(=O)_2OG^6$, $-S(=O)_2N(G^{6A})_2$, $-S(=O)G^5$, $-OC(=O)G^5$, $-OC(=O)N(G^{6A})_2$, $-NHC(=O)G^6$, $-OS(=O)_2G^5$, $-NHS(=O)_2G^5$ and $-C(=O)NHS(=O)_2G^5$; and

[substituent group (D1)]:

a halogen atom, a nitro group, a cyano group, $-G^5$, $-OG^{6A}$, $-SG^{6A}$, $-N(G^{6A})_2$, $-C(=O)G^6$, $-C(=O)OG^{6A}$, $-C(=O)N(G^{6A})_2$, $-S(=O)_2G^6$, $-S(=O)_2OG^6$, $S(=O)_2N(G^{6A})_2$, $-S(=O)G^5$, $-OC(=O)G^5$, $-OC(=O)N(G^{6A})_2$, $-NHC(=O)G^6$, $-OS(=O)_2G^5$, $-NHS(=O)_2G^5$ and $-C(=O)NHS(=O)_2G^5$;

in the substituent group (C1) and/or (D1), $G^5$ represents a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group;

$G^6$ represents a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group; and $G^{6A}$ represents a protective group, a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group, and with the proviso that $G^{6A}$ may be the same or different when there are 2 or more $G^{6A}$ in the substituents, or a pharmaceutically acceptable salt thereof; and the like.

In the present invention, the term "$C_{1-6}$ alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "$C_{2-6}$ alkenyl group" means a straight-chained or branched alkenyl group having 2 to 6 carbon atoms such as a vinyl group, an allyl group, a 1-propenyl group, an isopropenyl group, a 1-butenyl group, a 2-butenyl group, a 2-methylallyl group or the like; the term "$C_{2-6}$ alkynyl group" means a straight-chained or branched alkynyl group having 2 to 6 carbon atoms such as an ethynyl group, a 2-propynyl group or the like; the term "$C_{3-8}$ cycloalkyl group" means a cyclopropyl group a cyclobutyl group, a cyclopentyl group, a cyclohexyl group, a cycloheptyl group or a cyclooctyl group; the term "$C_{6-10}$ aryl group" means a phenyl group or a naphthyl group; the term "$C_{2-9}$ heterocycloalkyl group" means a 3 to 8-membered heterocycloalkyl group containing the same or different 1 or 2 hetero atoms other than the binding position selected from an oxygen atom, a sulfur atom and a nitrogen atom in the ring, which is derived from morpholine, thiomorpholine, tetrahydrofuran, tetrahydropyran, aziridine, azetidine, pyrrolidine, imidazolidine, oxazoline, piperidine, piperazine, pyrazolidine or the like, or a 5 o r 6-membered heterocycloalkyl group as defined above fused with an aliphatic or aromatic carbocycle or heterocycle such as a cyclohexane ring, a benzene ring, a pyridine ring or the like; the term "$C_{1-9}$ heteroaryl group" means a 5 or 6-membered heteroaryl group containing the same or different 1 to 4 hetero atoms other than the binding position selected from an oxygen atom, a sulfur atom and a nitrogen atom in the ring, which is derived from thiazole, oxazole, isothiazole, isoxazole, pyridine, pyrimidine, pyrazine, pyridazine, pyrrole, thiophene, imidazole, pyrazole, oxadiazole, thiodiazole, tetrazole, furazan or the like, or the above heteroaryl group fused with a 5 or 6-membered aromatic carbocycle or heterocycle such as a benzene ring, a pyrazole ring, a pyridine ring or the like; the term "aliphatic cyclic amino group" means a 3 to 8-membered aliphatic cyclic amino group which may have 1 or 2 unsaturated bond and may have a hetero atom selected from an oxygen atom, a sulfur atom and a nitrogen atom in the ring other than a nitrogen atom at the binding position, such as a morpholino group, a thiomorpholino group, a 1-aziridinyl group, a 1-azetidinyl group, a 1-pyrrolidinyl group, a piperidino group, a 1-imidazolidinyl group, a 1-piperadinyl group, a pyrazolidinyl group, a 1,2-dihydropyridin-1-yl group, a 1,4-dihydropyridin-1-yl group or the like; and the term "aromatic cyclic amino group" means a 5 or 6-membered aromatic cyclic amino group which may optionally have an oxo group as a substituent and may have 1 to 3 nitrogen atoms in the ring other than a nitrogen atom at the binding position, such as a 1-imidazolyl group, a 1-pyrrolyl group, a pyrazolyl group, a 1-tetrazolyl group, a 2-pyridon-1-yl group, a 4-pyridon-1-yl group, a 2-oxo-2H-pyrimidin-1-yl group, a 2-oxo-2H-pyrazin-1-yl group, a 2-oxo-6H-pyridazin-1-yl group, a 6-oxo-6H-[1,2,4,5]-tetradin-1-yl group or the like. The term "halogen atom" means a fluorine atom, a chlorine atom, a bromine atom or an iodine atom; the term "hydroxy-protective group" means a hydroxy-protective group used in general organic syntheses such as a benzyl group, a p-methoxybenzyl group, a p-nitrobenzyl group, a methoxymethyl group, an acetyl group, a tert-butyldimethylsilyl group, an allyl group, a benzoyl group, a pivaloyl group, a benzyloxycarbonyl group or the like; the term "thiol-protective group" means a thiol-protective group used in general organic syntheses such as a benzyl group, a p-methoxybenzyl group, a p-nitrobenzyl group, a triphenylmethyl group, a methoxymethyl group, an acetyl group, a benzoyl group, a pivaloyl group, a benzyloxycarbonyl group, an ethylaminocarbonyl group or the like; the term "amino-protective group" means an amino-protective group used in general organic syntheses such as a benzyloxycarbonyl group, a tert-butoxycarbonyl group, a benzyl group, a trifluoroacetyl group or the like; and the term "carboxy-protective group" means a carboxy-protective group used in general organic syntheses such as a benzyl group, a tert-butyldimethylsilyl group, an allyl group, a methyl group, an ethyl group or the like.

For example, the compounds represented by the above general formula (I) of the present invention can be prepared according to the following procedure:

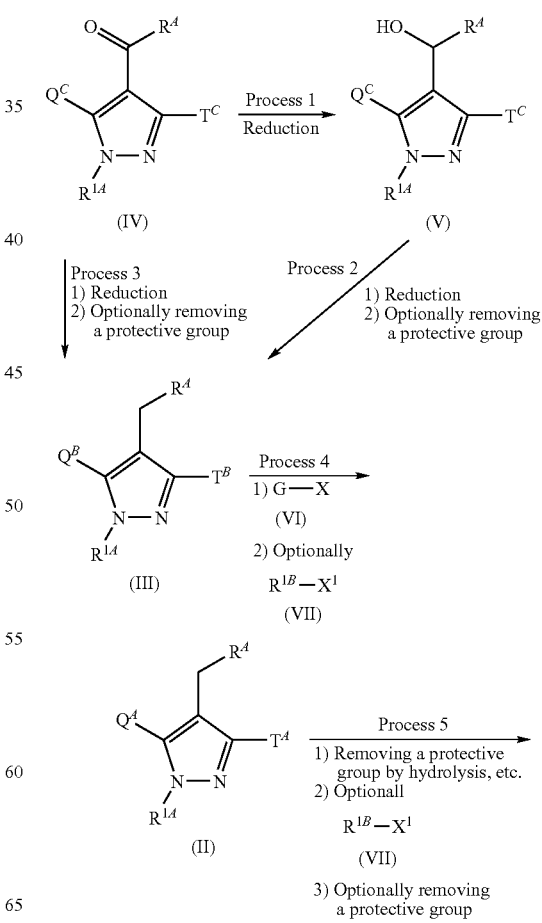

-continued

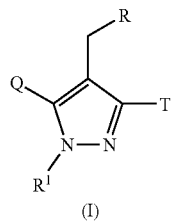
(I)

wherein one of $Q^C$ and $T^C$ represents a protected hydroxy group, and the other represents -$Z^A$-$Ar^A$ in which $Ar^A$ and $Z^A$ have the same meanings as defined above, an aliphatic cyclic amino group which may have the same or different 1 to 3 groups selected from the above substituent group (A1), or an aromatic cyclic amino group which may have the same or different 1 to 3 groups selected from the above substituent group (B1); G represents a group selected from β-D-glucopyranosyloxy group, a β-D-mannopyranosyloxy group, a α-D-glucopyranosyloxy group, a α-D-mannopyranosyloxy group, a β-D-2-deoxyglucopyranosyloxy group and a α-D-2-deoxyglucopyranosyloxy group, which has a hydroxy-protective group; X represents a leaving group such as a bromine atom or the like; $X^1$ represents a leaving group such as a halogen atom, a mesyloxy group, a tosyloxy group or the like; $R^{1B}$ represents a $C_{1-6}$ alkyl group which may have the same or different 1 to 3 groups selected from the above substituent group (A1), a $C_{2-6}$ alkenyl group which may have the same or different 1 to 3 groups selected from the above substituent group (A1), a $C_{2-6}$ alkynyl group which may have the same or different 1 to 3 groups selected from the above substituent group (A1), a $C_{3-8}$ cycloalkyl group which may have the same or different 1 to 3 groups selected from the above substituent group (A1), a $C_{6-10}$ aryl group which may have the same or different 1 to 3 groups selected from the above substituent group (B1), a $C_{2-9}$ heterocycloalkyl group which may have the same or different 1 to 3 groups selected from the above substituent group (A1), or a $C_{1-9}$ heteroaryl group which may have the same or different 1 to 3 groups selected from the above substituent group (B1); R, $R^1$, $R^{1A}$, $R^A$, Q, $Q^A$, $Q^B$, T, $T^A$ and $T^B$ have the same meanings as defined above.

Process 1

A compound represented by the above general formula (V) can be prepared by reducing a compound represented by the above general formula (IV) using a reducing agent such as sodium borohydride, diisobutylaluminum hydride, lithium aluminum hydride or the like in an inert solvent. As the inert solvent used, for example, toluene, tetrahydrofuran, dichloromethane, methanol, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process 2

A compound represented by the above general formula (III) of the present invention can be prepared by subjecting a compound represented by the general formula (V) to catalytic hydrogenation using a palladium catalyst such as palladium-carbon powder in the presence or absence of an acid such as hydrochloric acid in an inert solvent, or to reduction using a reducing agent such as triethylsillylhalide in the presence a Lewis acid such as trifluoroacetic acid and borontrifluoride diethyl ether complex without solvent or in an inert solvent and then optionally removing the hydroxy-protective group in the usual way. As the inert solvent used in the catalytic hydrogenation, for example, methanol, ethanol, tetrahydrofuran, ethyl acetate, acetic acid, a mixed solvent thereof and the like can be illustrated. The reaction temperature is usually from −78° C. to reflux temperature, and the reaction time is usually from 30 minutes to 1 day, varying based on a used starting material, solvent and reaction temperature. In addition, as the inert solvent used in the reduction using a reducing agent such as triethylsilly halide, for example, toluene, tetrahydrofuran, dichloromethane, a mixed solvent thereof and the like can be illustrated. The reaction temperature is usually from room temperature to reflux temperature, and the reaction time is usually from 30 minutes to 1 day, varying based on a used starting material, solvent and reaction temperature. The removal of a hydroxy-protective group can be conducted in various methods in the usual way, and in the case that the protective group is a benzyl group, for example, the reaction can be conducted in an aqueous solution of trifluoroacetic acid and dimethylsulfide usually at 0° C. to reflux temperature for 30 minutes to 1 day.

Process 3

A compound represented by the above general formula (III) of the present invention can be prepared by subjecting a compound represented by the above general formula (IV) to reduction using a reducing agent such as triethylsilyl halide in the presence of a Lewis acid such as trifluoroacetic acid and borontrifluoride diethyl ether complex without solvent or in an inert solvent and then optionally removing the hydroxy-protective group in the usual way. As the inert solvent used in the reduction, for example, toluene, tetrahydrofuran, dichloromethane, a mixed solvent thereof and the like can be illustrated. The reaction temperature is usually from room temperature to reflux temperature, and the reaction time is usually from 30 minutes to 1 day, varying based on a used starting material, solvent and reaction temperature.

Process 4

A compound represented by the above general formula (II) of the present invention can be prepared by subjecting a pyrazole derivative represented by the above general formula (III) to glycosidation using a sugar donor represented by the above general formula (VI) in the presence of a base such as sodium hydroxide, potassium hydroxide, potassium carbonate or the like and a phase transfer catalyst such as benzyltri(n-butyl)ammonium chloride, benzyltri(n-butyl)ammonium bromide, tetra(n-butyl)ammonium hydrogen sulfate or the like in water and an inert solvent and optionally to N-alkylation using an alkylating agent represented by the above general formula (VII) in the presence of a base such as cesium carbonate, potassium carbonate or sodium hydride and optionally in the presence of a catalytic amount of sodium iodide in an inert solvent. As the inert solvent used in the glycosidation, for example, dichloromethane, toluene, benzotrifluoride and the like can be illustrated. The reaction temperature is usually from 0° C. to reflux temperature, and the reaction time is usually from 30 minutes to 1 day, varying based on a used starting material, solvent and reaction temperature. As the solvent used in the N-alkylation, for example, acetonitrile, ethanol, 1,2-dimethoxyethane, tetrahydrofuran, N,N-dimethylformamide, N,N-dimethylacetamide, N-methylpyrrolidinone, dimethyl sulfoxide, a mixed solvent thereof and the like can be illustrated. The reaction temperature is usually from room temperature to reflux temperature, and the reaction time is usually from 10 minutes to 1 day, varying based on a used starting material, solvent and reaction temperature. The obtained compound represented by the above general formula (II) can be also used in the process 5 after converting into a salt thereof in the usual way.

Process 5

A compound represented by the above general formula (I) of the present invention can be prepared by subjecting a compound represented by the above general formula (II), after removing the protective group of sugar moiety or the like in accordance with a method used in general organic syntheses such as alkaline hydrolysis, optionally to N-Alkylation using an alkylating agent represented by the above general formula (VII) in the presence of a base such as cesium carbonate, potassium carbonate or sodium hydride and optionally in the presence of a catalytic amount of sodium iodide in an inert solvent, and in a case that there is a protective group other than the sugar moiety, by removing the protective group in accordance with a method used in general organic synthesis. As the inert solvent used in the hydrolysis reaction, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 10 minutes to 1 day, varying based on a used starting material, solvent and reaction temperature. As the solvent used in the N-alkylation, for example, acetonitrile, ethanol, 1,2-dimethoxyethane, tetrahydrofuran, N,N-dimethylformamide, N,N-dimethylacetamide, N-methylpyrrolidinone, dimethyl sulfoxide, a mixed solvent thereof and the like can be illustrated. The reaction temperature is usually from room temperature to reflux temperature, and the reaction time is usually from 10 minutes to 1 day, varying based on a used starting material, solvent and reaction temperature.

A compound represented by the above general formula (V) of the present invention used as a starting material in the above production processes, for example, can be prepared according to the following procedures:

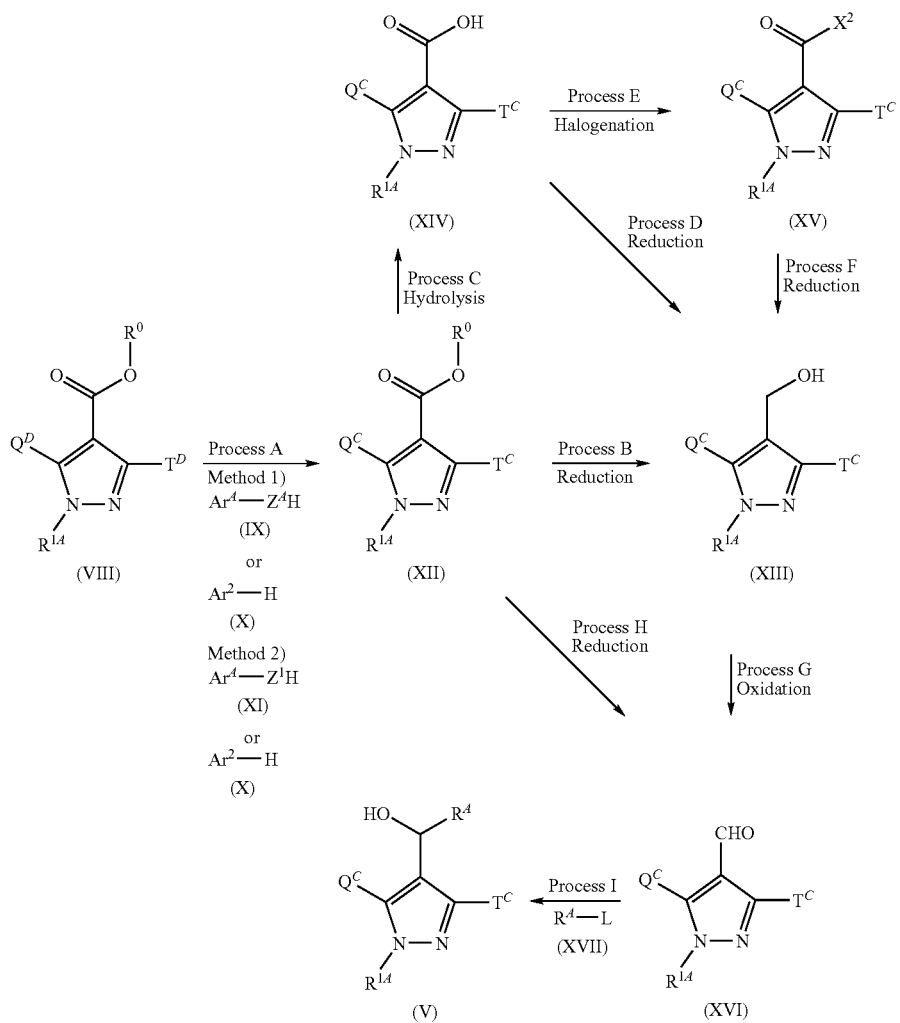

wherein one of $Q^D$ and $T^D$ represents a protected hydroxy group and the other represents a halogen atom; $R^0$ represents a $C_{1-6}$ alkyl group; $Ar^2$ represents an aliphatic cyclic amino group which may have the same or different 1 to 3 groups selected from the above substituent group (A1), or an aromatic cyclic amino group which may have the same or different 1 to 3 groups selected from the above substituent group (B1); L represents MgBr, MgCl, MgI, ZnI, ZnBr, ZnCl or a lithium atom; $X^2$ represents a halogen atom such as a bromine atom, a chlorine atom or the like; $Z^1$ represents —$NY^A$— wherein $Y^A$ represents a hydrogen atom, a $C_{1-6}$ alkyl group or a protective group; $Ar^A$, $R^{1A}$, $R^A$, $Q^C$, $T^C$ and $Z^A$ have the same meanings as defined above.

Process A

A compound represented by the above general formula (XII) can be prepared by subjecting a compound represented by the above general formula (VIII) (method 1) to condensation with a compound represented by the above general formula (IX) or (X) in the presence or absence of a base such as sodium hydride, potassium carbonate or the like in an inert solvent, or (method 2) to condensation with a compound represented by the above general formula (XI) or (X) using a catalyst such as tris(dibenzylideneacetone)dipalladium and a ligand such as 2,2'-bis(diphenylphosphino)-1,1'-binaphthyl in the presence of a base such as cesium carbonate, sodium tert-butoxide in an inert solvent. As the inert solvent used in the method 1, for example, N,N-dimethylacetamide, toluene, tetrahydrofuran, a mixed solvent thereof and the like can be illustrated. The reaction temperature is usually from room temperature to reflux temperature, and the reaction time is usually from 1 hour to 1 day, varying based on a used starting material, solvent and reaction temperature. In addition, as the inert solvent used in the method 2, for example, N,N-dimethylacetamide, toluene, tetrahydrofuran, a mixed solvent thereof and the like can be illustrated. The reaction temperature is usually from room temperature to reflux temperature, and the reaction time is usually from 1 hour to 1 day, varying based on a used starting material, solvent and reaction temperature.

Process B

A compound represented by the general formula (XIII) can be prepared by reducing a compound represented by the above general formula (XII) using a reducing agent such as lithium aluminum hydride, diisobutylaluminum hydride or the like in an inert solvent. As the inert solvent used in the reduction, for example, toluene, tetrahydrofuran, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process C

A compound represented by the above general formula (XIV) can be prepared by treating a compound represented by the above general formula (XII) according to a method used in general organic syntheses such as alkaline hydrolysis. As the solvent used in the hydrolysis reaction, for example, methanol, ethanol, acetonitrile, tetrahydrofuran, dioxane, water, a mixed solvent thereof and the like can be illustrated. As the base, for example, sodium hydroxide, sodium methoxide, sodium ethoxide and the like can be illustrated. The reaction temperature is usually from room temperature to reflux temperature, and the reaction time is usually from 30 minutes to 1 day, varying based on a used starting material, solvent and reaction temperature.

Process D

A compound represented by the above general formula (XIII) can be prepared by subjecting a compound represented by the above general formula (XIV) to reduction using a reducing agent such as lithium aluminum hydride, borane-dimethylsulfide complex or borane-tetrahydrofuran complex in an inert solvent. As the inert solvent used in the reduction, for example, toluene, tetrahydrofuran, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process E

A compound represented by the above general formula (XV) can be prepared by halogenating a compound represented by the above general formula (XIV) using an acid halide reagent such as thionyl chloride, phosphorus trichloride, phosphorus pentachloride, phosphorus oxychloride, phosphorus tribromide or fluorosulfuric acid without solvent or in an inert solvent. As the inert solvent used in the halogenation, for example, toluene, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process F

A compound represented by the above general formula (XIII) can be prepared by subjecting a compound represented by the above general formula (XV) to reduction using a reducing agent such as lithium aluminum hydride, sodium borohydride or lithium borohydride in an inert solvent. As the inert solvent used in the reduction, for example, toluene, tetrahydrofuran, dichloromethane, ethanol, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process G

A compound represented by the above general formula (XVI) can be prepared by subjecting a compound represented by the above general formula (XIII) to oxidation using dimethylsulfoxide such as Swern oxidation, chromic acid oxidation using pyridinium chlorochromate, pyridinium dichromate or the like in an inert solvent or oxidation using an oxidant such as manganese dioxide. As the inert solvent used in the above oxidation, for example, toluene, tetrahydrofuran, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process H

A compound represented by the above general formula (XVI) can be prepared by subjecting a compound represented by the above general formula (XII) to reduction using a reducing agent such as triisopropoxyalminum hydride or diisobutylaluminum hydride in an inert solvent. As the inert solvent used in the reduction, for example, toluene, tetrahydrofuran, hexane, diethyl ether, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process I

A compound represented by the above general formula (V) can be prepared by condensing a compound represented by the above general formula (XVI) with a Grignard reagent, a Reformatsky reagent or a lithium reagent represented by the above general formula (XVII) in an inert solvent. As the inert solvent used in the condensing reaction, for example, tetrahydrofuran, diethyl ether, a mixed solvent thereof and the like can be illustrated. The reaction temperature is usually from −78° C. to room temperature, and the reaction time is usually from 30 minutes to 1 day, varying based on a used starting material, solvent and reaction temperature.

A compound represented by the above general formula (IV) of the present invention used as a starting material in the above production processes, for example, can be prepared according to the following procedures:

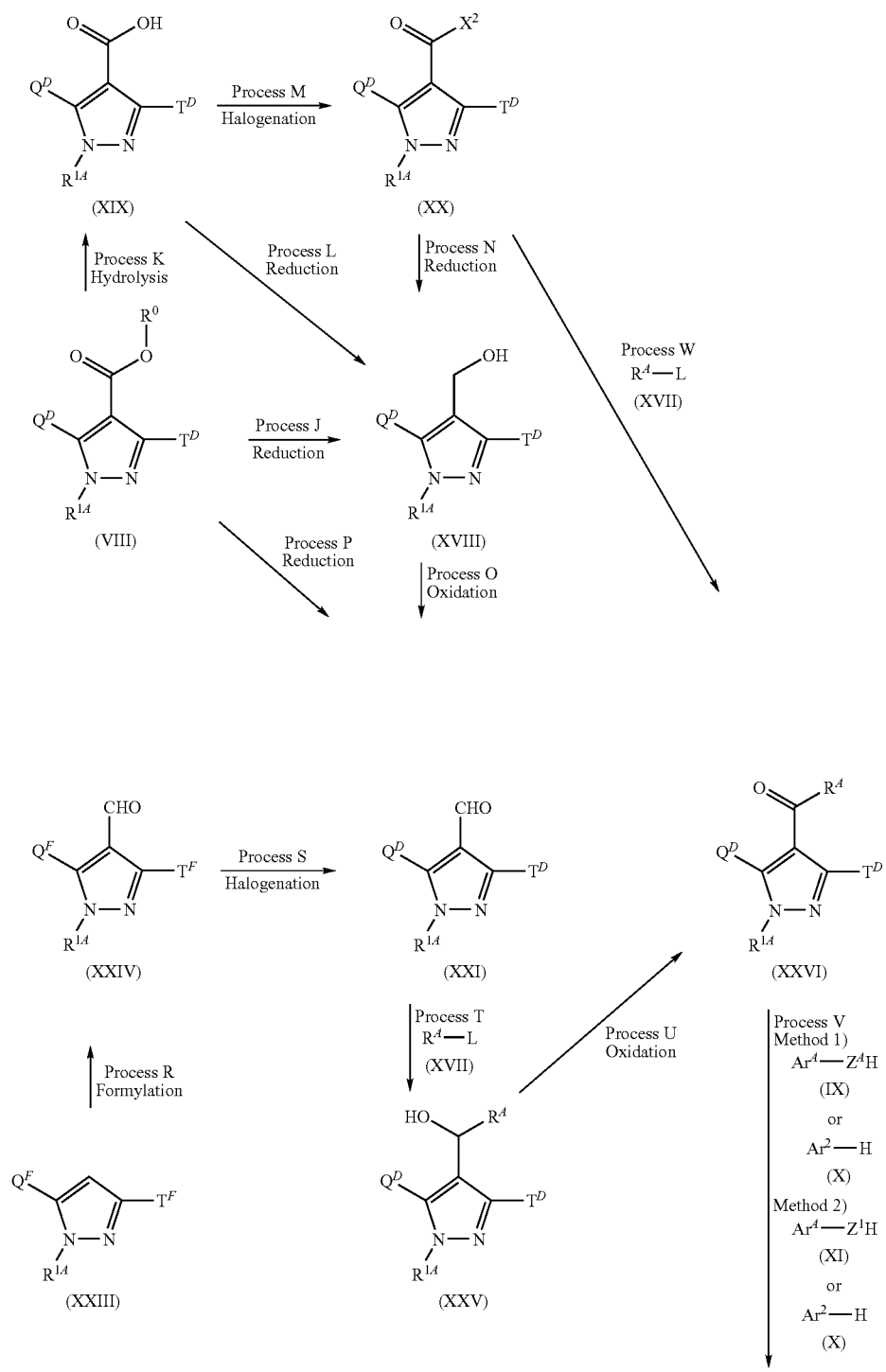

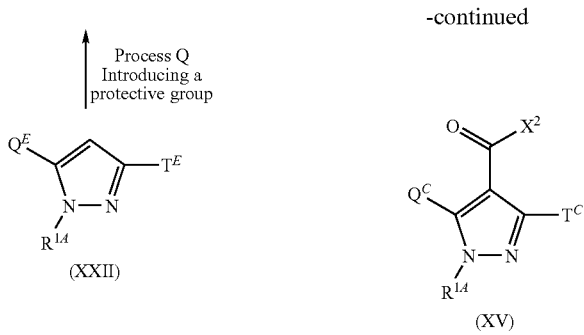

-continued wherein one of $Q^E$ and $T^E$ represents a hydroxy group and the other represents a hydrogen atom; one of $Q^F$ and $T^F$ represents a protected hydroxy group and the other represents a hydrogen atom; $Ar^1$, $Ar^2$, L, $R^{14}$, $R^0$, $R^A$, $Q^C$, $Q^D$, $T^C$, $T^D$, $X^2$, $Z^A$ and $Z^1$ have the same meanings as defined above.

Process J

A compound represented by the general formula (XVIII) can be prepared by reducing a compound represented by the above general formula (VIII) using a reducing agent such as lithium aluminum hydride, diisobutylaluminum hydride or the like in an inert solvent. As the inert solvent used in the reduction, for example, toluene, tetrahydrofuran, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process K

A compound represented by the above general formula (XIX) can be prepared by treating a compound represented by the above general formula (VIII) according to a method used in general organic syntheses such as alkaline hydrolysis. As the solvent used in the hydrolysis reaction, for example, methanol, ethanol, acetonitrile, tetrahydrofuran, dioxane, water, a mixed solvent thereof and the like can be illustrated. As the base, for example, sodium hydroxide, sodium methoxide, sodium ethoxide, potassium hydroxide and the like can be illustrated. The reaction temperature is usually from room temperature to reflux temperature, and the reaction time is usually from 30 minutes to 1 day, varying based on a used starting material, solvent and reaction temperature.

Process L

A compound represented by the above general formula (XVIII) can be prepared by subjecting a compound represented by the above general formula (XIX) to reduction using a reducing agent such as lithium aluminum hydride, borane-dimethylsulfide complex or borane-tetrahydrofuran complex in an inert solvent. As the inert solvent used in the reduction, for example, toluene, tetrahydrofuran, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process M

A compound represented by the above general formula (XX) can be prepared by halogenating a compound represented by the above general formula (XIX) using an acid halide reagent such as thionyl chloride, phosphorus trichloride, phosphorus pentachloride, phosphorus oxychloride, phosphorus tribromide or fluorosulfuric acid without solvent or in an inert solvent. As the inert solvent used in the halogenation, for example, toluene, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process N

A compound represented by the above general formula (XVIII) can be prepared by subjecting a compound represented by the above general formula (XX) to reduction using a reducing agent such as lithium aluminum hydride, sodium borohydride or lithium borohydride in an inert solvent. As the inert solvent used in the reduction, for example, toluene, tetrahydrofuran, dichloromethane, ethanol, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process O

A compound represented by the above general formula (XXI) can be prepared by subjecting a compound represented by the above general formula (XVIII) to oxidation using dimethylsulfoxide such as Swern oxidation, chromic acid oxidation using pyridinium chlorochromate, pyridinium dichromate or the like in an inert solvent or oxidation using an oxidant such as manganese dioxide. As the inert solvent used in the above oxidation, for example, toluene, tetrahydrofuran, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process P

A compound represented by the above general formula (XXI) can be prepared by subjecting a compound represented by the above general formula (VIII) to reduction using a reducing agent such as triisopropoxyalminum hydride or diisobutylaluminum hydride in an inert solvent. As the inert solvent used in the reduction, for example, toluene, tetrahydrofuran, hexane, diethyl ether, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process Q

A compound represented by the above general formula (XXIII) can be prepared by introducing a protective group into a hydroxy group of a compound represented by the above general formula (XXII) using an agent for protecting a hydroxy group such as benzyl bromide, chloromethyl methyl ether or the like in the presence of a base such as sodium hydroxide, potassium carbonate or the like and a phase transfer catalyst such as benzyltri(n-butyl)ammonium chloride, benzyltri(n-butyl)ammonium bromide or the like in water and an inert solvent. As the inert solvent used in the introducing reaction, for example, toluene, tetrahydrofuran, dichloromethane, a mixed solvent thereof and the like can be illustrated. The reaction temperature is usually from 0° C. to reflux temperature, and the reaction time is usually from 30 minutes to 1 day, varying based on a used starting material, solvent and reaction temperature.

Process R

A pyrazole aldehyde derivative represented by the above general formula (XXIV) can be prepared by subjecting a compound represented by the above general formula (XXIII) to formylation by a reaction such as Vilsmeier reaction using phosphorus oxychloride and N,N-dimethylformamide. As the solvent used in the formylating reaction, for example, N,N-dimethylformamide and the like can be illustrated. The reaction temperature is usually from 0° C. to reflux temperature, and the reaction time is usually from 30 minutes to 1 day, varying based on a used starting material, solvent and reaction temperature.

Process S

A compound represented by the above general formula (XXI) can be prepared by halogenating a compound represented by the above general formula (XXIV) using a halogenating agent such as bromine or iodine after treating with a base such as n-butyllithium in an inert solvent. The formyl group can be optionally derived into dimethylacetal, 1,3-dioxolane or the like, and then deprotected after halogenation. As the inert solvent used in the halogenation, for example, toluene, tetrahydrofuran, a mixed solvent thereof and the like can be illustrated. The reaction temperature is usually from −78° C. to reflux temperature, and the reaction time is usually from 10 minutes to 1 day, varying based on a used starting material, solvent and reaction temperature.

Process T

A compound represented by the above general formula (XXV) can be prepared by condensing a compound represented by the above general formula (XXI) with a Grignard reagent, a Reformatsky reagent or a lithium reagent represented by the above general formula (XVII) in an inert solvent. As the inert solvent used in the condensing reaction, for example, tetrahydrofuran, diethyl ether, a mixed solvent thereof and the like can be illustrated. The reaction temperature is usually from −78° C. to room temperature, and the reaction time is usually from 30 minutes to 1 day, varying based on a used starting material, solvent and reaction temperature.

Process U

A compound represented by the above general formula (XXVI) can be prepared by subjecting a compound represented by the above general formula (XXV) to oxidation using dimethylsulfoxide such as Swern oxidation, chromic acid oxidation using pyridinium chlorochromate, pyridinium dichromate or the like in an inert solvent or oxidation using an oxidant such as manganese dioxide. As the inert solvent used in the above oxidation, for example, toluene, tetrahydrofuran, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process V

A compound represented by the above general formula (IV) can be prepared by subjecting a compound represented by the above general formula (XXVI) (method 1) to condensation with a compound represented by the above general formula (IX) or (X) in the presence or absence of a base such as sodium hydride, potassium carbonate or the like in an inert solvent, or (method 2) to condensation with a compound represented by the above general formula (XI) or (X) using a catalyst such as tris(dibenzylideneacetone)dipalladium and a ligand such as 2,2'-bis(diphenylphosphino)-1,1'-binaphthyl in the presence of a base such as cesium carbonate, sodium tert-butoxide in an inert solvent. As the inert solvent used in the method 1, for example, N,N-dimethylacetamide, toluene, tetrahydrofuran, a mixed solvent thereof and the like can be illustrated. The reaction temperature is usually from room temperature to reflux temperature, and the reaction time is usually from 1 hour to 1 day, varying based on a used starting material, solvent and reaction temperature. In addition, as the inert solvent used in the method 2, for example, N,N-dimethylacetamide, toluene, tetrahydrofuran, a mixed solvent thereof and the like can be illustrated. The reaction temperature is usually from room temperature to reflux temperature, and the reaction time is usually from 1 hour to 1 day, varying based on a used starting material, solvent and reaction temperature.

Process W

A compound represented by the above general formula (XXVI) can be prepared by condensing a compound represented by the above general formula (XX) with a Grignard reagent, a Reformatsky reagent or a lithium reagent represented by the above general formula (XVII) in an inert solvent. As the inert solvent used in the condensing reaction, for example, tetrahydrofuran, diethyl ether, a mixed solvent thereof and the like can be illustrated. The reaction temperature is usually from −78° C. to room temperature, and the reaction time is usually from 30 minutes to 1 day, varying based on a used starting material, solvent and reaction temperature.

Process X

A compound represented by the above general formula (IV) can be prepared by condensing a compound represented by the above general formula (XV) with a Grignard reagent, a Reformatsky reagent or a lithium reagent represented by the above general formula (XVII) in an inert solvent. As the inert solvent used in the condensing reaction, for example, tetrahydrofuran, diethyl ether, a mixed solvent thereof and the like can be illustrated. The reaction temperature is usually from −78° C. to room temperature, and the reaction time is usually from 30 minutes to 1 day, varying based on a used starting material, solvent and reaction temperature.

A compound represented by the above general formula (VIII) of the present invention used as a starting material in the above production processes, for example, can be prepared according to the following procedures:

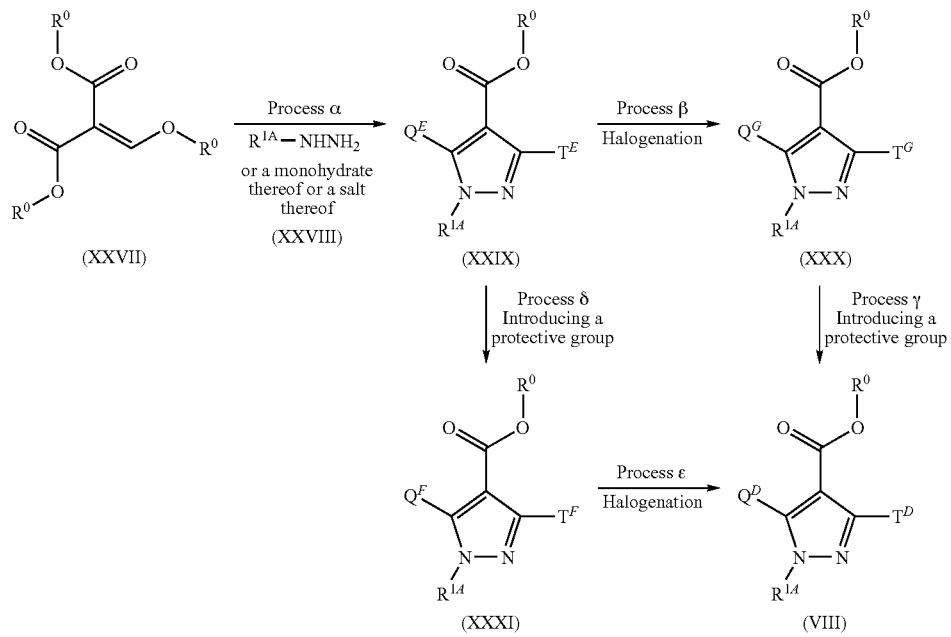

wherein one of $Q^G$ and $T^G$ represents a hydroxy group and the other represents a halogen atom; $R^0$, $R^{1A}$, $Q^D$, $Q^E$, $Q^F$, $T^D$, $T^E$ and $T^F$ have the same meanings as defined above.

Process α

A pyrazole derivative represented by the above general formula (XXIX) can be prepared by subjecting a compound represented by the above general formula (XXVII) to condensation with a hydrazine compound or a hydrate thereof or a salt thereof in the presence or absence of a base in an inert solvent. As the inert solvent used in the condensation, for example, toluene, tetrahydrofuran, dichloromethane, N,N-dimethylformamide, ethanol, water, a mixed solvent thereof and the like can be illustrated. As the base, for example, sodium hydride, sodium amide, sodium carbonate, sodium ethoxide and the like can be illustrated. The reaction temperature is usually from room temperature to reflux temperature, and the reaction time is usually from 10 minutes to 1 day, varying based on a used starting material, solvent and reaction temperature.

Process β

A compound represented by the above general formula (XXX) can be prepared by halogenating a compound represented by the above general formula (XXIX) using a halogenating agent such as sulfuryl chloride, N-chlorosuccinimide or N-bromosuccinimide in an inert solvent. As the inert solvent used in the halogenation, for example, tetrahydrofuran, dichloromethane, acetic acid, toluene, N,N-dimethylformamide, a mixed solvent thereof and the like can be illustrated. The reaction temperature is usually from 0° C. to reflux temperature, and the reaction time is usually from 10 minutes to 1 day, varying based on a used starting material, solvent and reaction temperature.

Process γ

A compound represented by the above general formula (VIII) can be prepared by introducing a hydroxy-protective group to a compound represented by the above general formula (XXX) using a hydroxy-protecting agent such as benzylbromide or chloromethyl methyl ether in the presence or absence of a base in an inert solvent. As the inert solvent used in the introducing reaction, for example, toluene, tetrahydrofuran, dichloromethane, N,N-dimethylformamide, ethanol, water, a mixed solvent thereof and the like can be illustrated. As the base, for example, sodium hydride, sodium amide, sodium carbonate, sodium ethoxide, triethylamine, imidazole and the like can be illustrated. The reaction temperature is usually from 0° C. to reflux temperature, and the reaction time is usually from 10 minutes to 1 day, varying based on a used starting material, solvent and reaction temperature.

Process δ

A compound represented by the above general formula (XXXI) can be prepared by introducing a hydroxy-protective group to a compound represented by the above general formula (XXIX) using a hydroxy-protecting agent such as benzyl bromide or chloromethyl methyl ether in the presence or absence of a base in an inert solvent. As the inert solvent used in the introducing reaction, for example, toluene, tetrahydrofuran, dichloromethane, N,N-dimethylformamide, ethanol, water, a mixed solvent thereof and the like can be illustrated. As the base, for example, sodium hydride, sodium amide, sodium carbonate, sodium ethoxide, triethylamine, imidazole and the like can be illustrated. The reaction temperature is usually from 0° C. to reflux temperature, and the reaction time is usually from 10 minutes to 1 day, varying based on a used starting material, solvent and reaction temperature.

Process ε

A compound represented by the above general formula (VIII) can be prepared by halogenating a compound represented by the above general formula (XXXI) using a halogenating agent such as bromine or iodine after treating with a base such as n-butyllithium in an inert solvent. As the inert solvent used in the halogenation, for example, toluene, tetrahydrofuran, a mixed solvent thereof and the like can be illustrated. The reaction temperature is usually from −78° C. to reflux temperature, and the reaction time is usually from 10 minutes to 1 day, varying based on a used starting material, solvent and reaction temperature.

In the compounds represented by the above general formula (III) of the present invention, there can be the several tautomers such as a pyrazolone compound, and any of the compounds are included in the present invention. In addition, in some of the starting materials, there also can be several tautomers such as a pyrazolone compound, varying based on difference in the existence condition.

The compounds represented by the above general formula (I) of the present invention obtained by the above production processes can be isolated and purified by conventional separation means such as fractional recrystallization, purification using chromatography, solvent extraction and solid phase extraction.

The pyrazole derivatives represented by the above general formula (I) of the present invention can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like, salts with inorganic bases such as a sodium salt, a potassium salt and the like, and salts with organic bases such as N-methyl-D-glucamine, N,N'-dibenzyletylenediamine, 2-aminoethanol, tris (hydroxymethyl)aminomethane, arginine, lysine and the like.

The compounds represented by the above general formula (I) of the present invention or pharmaceutically acceptable salts thereof, or prodrugs thereof include their solvates with pharmaceutically acceptable solvents such as ethanol and water.

Of the pyrazole derivatives represented by the above general formula (I) of the present invention and the prodrugs thereof, there are two geometrical isomers in each compound having an unsaturated bond. In the present invention, either of cis(Z)-isomer or trans(E)-isomer can be employed.

Of the pyrazole derivatives represented by the above general formula (I) of the present invention and the prodrugs thereof, there are two optical isomers, R-isomer and S-isomer, in each compound having an asymmetric carbon atom excluding the sugar moiety of glucopyranosyloxy, mannopyranosyloxy and 2-deoxyglucopyranosyloxy moieties. In the present invention, either of the optical isomers can be employed, and a mixture of both optical isomers can be also employed. In addition, there can be two rotational isomers in each compound having a rotational barrier. In the present invention, either of the rotational isomers can be employed, and a mixture of both rotational isomers can be also employed.

A prodrug of a compound represented by the above general formula (I) of the present invention can be prepared by introducing an appropriate group forming a prodrug into any one or more groups selected from a hydroxy group, an amino group and a sulfonamide group of the compound represented by the above general formula (I) using a corresponding reagent to produce a prodrug such as a halide compound or the like in the usual way, and then by suitably isolating and purificating in the usual way as occasion demands. As a group forming a prodrug used in a hydroxy group, for example, a $C_{2-20}$ acyl group, a $C_{1-6}$ alkoxy-substituted ($C_{2-7}$ acyl) group, a $C_{2-7}$ alkoxycarbonyl-substituted ($C_{2-7}$ acyl) group, a $C_{2-7}$ alkoxycarbonyl group, a $C_{1-6}$ alkoxy-substituted ($C_{2-7}$ alkoxycarbonyl) group, a benzoyl group, a ($C_{2-7}$ acyloxy) methyl group, a 1-($C_{2-7}$ acyloxy)ethyl group, a ($C_{2-7}$ alkoxycarbonyl)oxymethyl group, a 1-[($C_{2-7}$ alkoxycarbonyl)oxy] ethyl group, a ($C_{3-7}$ cycloalkyl)oxycarbonyloxymethyl group, a 1-[($C_{3-7}$ cycloalkyl)oxycarbonyloxy]ethyl group, an ester group condensed with an amino acid, a phosphoric acid derivative or a cinnamic acid derivative or the like can be illustrated. As a group forming a prodrug used in an amino group, for example, a $C_{2-7}$ acyl group, a $C_{1-6}$ alkoxy-substituted ($C_{2-7}$ acyl) group, a $C_{2-7}$ alkoxycarbonyl-substituted ($C_{2-7}$ acyl) group, a $C_{2-7}$ alkoxycarbonyl group, a $C_{1-6}$ alkoxy-substituted ($C_{2-7}$ alkoxycarbonyl) group, a benzoyl group, a ($C_{2-7}$ acyloxy)methyl group, a 1-($C_{2-7}$ acyloxy)ethyl group, a ($C_{2-7}$ alkoxycarbonyl)oxymethyl group, a 1-[($C_{2-7}$ alkoxycarbonyl)oxy]ethyl group, a ($C_{3-7}$ cycloalkyl)oxycarbonyloxymethyl group, a 1-[($C_{3-7}$ cycloalkyl)oxycarbonyloxy] ethyl group, an amide group condensed with an amino acid or the like can be illustrated. As a group forming a prodrug used in a sulfonamide group, for example, a ($C_{2-7}$ acyloxy)methyl group, a 1-($C_{2-7}$ acyloxy)ethyl group, a ($C_{2-7}$ alkoxycarbonyl) oxymethyl group, a 1-[($C_{2-7}$ alkoxycarbonyl)oxy]ethyl group, a ($C_{3-7}$ cycloalkyl)oxycarbonyloxymethyl group, a 1-[($C_{3-7}$ cycloalkyl)oxycarbonyloxy]ethyl group or the like can be illustrated. The term "$C_{2-7}$ acyl group" means a straight-chained or branched acyl group having 2 to 7 carbon atoms such as an acetyl group, a propionyl group, a butyryl group, an isobutyryl group, a valeryl group, a pivaloyl group, a hexanoyl group or the like; the term "$C_{2-20}$ acyl group" means a straight-chained or branched acyl group having 2 to 20 carbon atoms such as an acetyl group, a propionyl group, a butyryl group, an isobutyryl group, a valeryl group, a pivaloyl group, a hexanoyl group, a lauroyl group, a myristoyl group, a palmitoyl group, a stearoyl group or the like; the term "$C_{1-6}$ alkoxy-substituted ($C_{2-7}$ acyl) group" means the above $C_{2-7}$ acyl group substituted by a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; the term "$C_{2-7}$ alkoxycarbonyl group" means a straight-chained or branched alkoxycarbonyl group having 2 to 7 carbon atoms such as a methoxycarbonyl group, an ethoxycarbonyl group, a propoxycarbonyl group, an isopropoxycarbonyl group, a butoxycarbonyl group, an isobutyloxycarbonyl group, a sec-butoxycarbonyl group, a tert-butoxycarbonyl group, a pentyloxycarbonyl group, an isopentyloxycarbonyl group, a neopentyloxycarbonyl group, a tert-pentyloxycarbonyl group, a hexyloxycarbonyl group or the like or a cyclic alkoxycarbonyl group having a 3 to 6-membered cycloalkyl group such as a cyclopropyloxycarbonyl group, a cyclobutyloxycarbonyl group, a cyclopentyloxycarbonyl group, a cyclohexyloxycarbonyl group or the like; the term "$C_{2-7}$ alkoxycarbonyl-substituted ($C_{2-7}$ acyl) group" means the above $C_{2-7}$ acyl group substituted by the above $C_{2-7}$ alkoxycarbonyl group; the term "$C_{1-6}$ alkoxy-substituted ($C_{2-7}$ alkoxycarbonyl) group" means the above $C_{2-7}$ alkoxycarbonyl group substituted by the above $C_{1-6}$ alkoxy group; the term "($C_{2-7}$ acyloxy)methyl group" means a hydroxymethyl group O-substituted by the above $C_{2-7}$ acyl group; the term "1-($C_{2-7}$ acyloxy)ethyl group" means a 1-hydroxyethyl group O-substituted by the above $C_{2-7}$ acyl group; the term "($C_{2-7}$ alkoxycarbonyl)oxymethyl group" means a hydroxymethyl group O-substituted by the above $C_{2-7}$ alkoxycarbonyl group; and the term "1-[($C_{2-7}$ alkoxycarbonyl)oxy]ethyl group" means a 1-hydroxyethyl group O-substituted by the above $C_{2-7}$ alkoxycarbonyl group. In addition, the term "($C_{3-7}$ cycloalkyl)oxycarbonyl group" means an ester group having the above $C_{3-7}$ cycloalkyl group; the term "($C_{3-7}$ cycloalkyl)oxycarbonyloxymethyl group" means a hydroxymethyl group O-substituted by the above ($C_{3-7}$ cycloalkyl)oxycarbonyl group; and the term "1-[($C_{3-7}$ cycloalkyl)oxycarbonyloxy]ethyl group" means a 1-hydroxyethyl group O-substituted by the above ($C_{3-7}$ cycloalkyl)oxycarbonyl group. Furthermore, as a group forming a prodrug, a sugar residue of a glucopyranosyl group, a galactopyranosyl group or the like can be illustrated. For example, these groups are preferably introduced into the hydroxy group at the 4 or 6 position of the sugar moiety of glucopyranosyloxy group or the like.

The pyrazole derivatives represented by the above general formula (I) of the present invention, for example, showed a potent inhibitory activity in human SGLT inhibitory activity confirmatory test as described below. Thus, the pyrazole derivatives represented by the above general formula (I) of the present invention can remarkably inhibit blood glucose level increase by inhibiting the reabsorption or uptake into cells of glucose, mannose and/or fructose at the kidney or inhibiting their sugar absorption at the small intestine. Therefore, a pyrazole derivative represented by the above general formula (I) of the present invention, a pharmaceutically acceptable salt and a prodrug thereof is useful as an agent for the prevention, inhibition of progression or treatment of a disease associated with the excess uptake of at least a kind of carbohydrates selected from glucose, fructose and mannose, such as diabetes, postprandial hyperglycemia, impaired glucose tolerance, diabetic complications (e.g., retinopathy, neuropathy, nephropathy, ulcer, macroangiopathy), obesity, hyperinsulinemia, hyperlipidemia, hypercholesterolemia, hypertriglyceridemia, lipid metabolism disorder, atherosclerosis, hypertension, congestive heart failure, edematous state, metabolic acidosis, syndrome X, hyperuricemia, gout, nephritis or the like, specially useful for the prevention, inhibition of progression or treatment of a disease associated with hyperglycemia.

Furthermore, the compounds of the present invention can be suitably used in combination with other drugs. Examples of the drugs which can be used in combination with the compounds of the present invention include an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor (PDGF), a platelet-derived growth factor (PDGF) analogue (e.g., PDGF-AA, PDGF-BB, PDGF-AB), epidermal growth factor (EGF), nerve growth factor, a carnitine derivative, uridine, 5-hydroxy-1-methylhydantoin, EGB-761, bimoclomol, sulodexide, Y-128, a hydroxymethylglutaryl coenzyme A reductase inhibitor, a fibric acid derivative, a $β_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyltransferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an anti-platelets agent, a uric acid synthesis inhibitor, a uricosuric agent and a urinary alkalinizer.

In case of uses of the compound of the present invention in combination with the above one or more drugs, the present invention includes either dosage forms of simultaneous administration as a single preparation or separated preparations in way of the same or different administration route, and administration at different dosage intervals as separated preparations in way of the same or different administration route. A pharmaceutical combination comprising the compound of the present invention and the above drug(s) includes both dosage forms as a single preparation and separated preparations for combination as mentioned above.

The compounds of the present invention can obtain more advantageous effects than additive effects in the prevention or treatment of the above diseases when using suitably in combination with the above one or more drugs. Also, the administration dose can be decreased in comparison with administration of either drug alone, or adverse effects of other coadministrated drugs can be avoided or declined.

Concrete compounds as the drugs used for combination and preferable diseases to be treated are exemplified as follows. However, the present invention is not limited thereto, and the concrete compounds include their free compounds, and their or other pharmaceutically acceptable salts.

As insulin sensitivity enhancers, peroxisome proliferator-activated receptor-γ agonists such as troglitazone, pioglitazone hydrochloride, rosiglitazone maleate, sodium darglitazone, GI-262570, isaglitazone, LG-100641, NC-2100, T-174, DRF-2189, CLX-0921, CS-011, GW-1929, ciglitazone, sodium englitazone and NIP-221, peroxisome proliferator-activated receptor-α agonists such as GW-9578 and BM-170744, peroxisome proliferator-activated receptor-α/γ agonists such as GW-409544, KRP-297, NN-622, CLX-0940, LR-90, SB-219994, DRF-4158 and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-H049020 and GW-501516 are illustrated. Insulin sensitivity enhancers are used preferably for diabetes, impaired glucose tolerance, diabetic complications, obesity, hyperinsulinemia, hyperlipidemia, hypercholesterolemia, hypertriglyceridemia, lipid metabolism disorder or atherosclerosis, and more preferably for diabetes, impaired glucose tolerance or hyperinsulinemia because of improving the disturbance of insulin signal transduction in peripheral tissues and enhancing glucose uptake into the tissues from the blood, leading to lowering of blood glucose level.

As glucose absorption inhibitors, for example, α-glucosidase inhibitors such as a carbose, voglibose, miglitol, CKD- 711, emiglitate, MDL-25,637, camiglibose and MDL-73,945, α-amylase inhibitors such as AZM-127, and SGLT1 inhibitors are illustrated. Glucose absorption inhibitors are used preferably for diabetes, impaired glucose tolerance, diabetic complications, obesity or hyperinsulinemia, and more preferably for impaired glucose tolerance because of inhibiting the gastrointestinal enzymatic digestion of carbohydrates contained in foods, and inhibiting or delaying the absorption of glucose into the body.

As biguanides, phenformin, buformin hydrochloride, metformin hydrochloride or the like are illustrated. Biguanides are used preferably for diabetes, impaired glucose tolerance, diabetic complications or hyperinsulinemia, and more preferably for diabetes, impaired glucose tolerance or hyperinsulinemia because of lowering blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlorpropamide, tolazamide, acetohexamide, glyclopyramide, glyburide (glibenclamide), gliclazide, 1-butyl-3-metanilylurea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide or the like are illustrated. Insulin secretion enhancers are used preferably for diabetes, impaired glucose tolerance or diabetic complications, and more preferably for diabetes or impaired glucose tolerance because of lowering blood glucose level by acting on pancreatic β-cells and enhancing the insulin secretion.

As SGLT2 inhibitors, T-1095 and compounds described in Japanese patent publications Nos. Hei10-237089 and 2001-288178, and International Publications Nos. WO01/16147, WO01/27128, WO01/68660, WO01/74834, WO01/74835, WO02/28872, WO02/36602, WO02/44192, WO02/053573, WO02/064606, WO02/068439, WO02/068440 or the like are illustrated. SGLT2 inhibitors are used preferably for diabetes, impaired glucose tolerance, diabetic complications, obesity or hyperinsulinemia, and more preferably for diabetes, impaired glucose tolerance, obesity or hyperinsulinemia because of lowering blood glucose level by inhibiting the reabsorption of glucose at renal proximal tubule.

As insulin or insulin analogues, human insulin, animal-derived insulin, human or animal-derived insulin analogues or the like are illustrated. These preparations are used preferably for diabetes, impaired glucose tolerance or diabetic complications, and more preferably for diabetes or impaired glucose tolerance.

As glucagon receptor antagonists, BAY-27-9955, NNC-92-1687 or the like are illustrated; as insulin receptor kinase stimulants, TER-17411, L-783281, KRX-613 or the like are illustrated; as tripeptidyl peptidase II inhibitors, UCL-1397 or the like are illustrated; as dipeptidyl peptidase IV inhibitors, NVP-DPP728A, TSL-225, P-32/98 or the like are illustrated; as protein tyrosine phosphatase 1B inhibitors, PTP-112, OC-86839, PNU-177496 or the like are illustrated; as glycogen phosphorylase inhibitors, NN-4201, CP-368296 or the like are illustrated; as fructose-bisphosphatase inhibitors, R-132917 or the like are illustrated; as pyruvate dehydrogenase inhibitors, AZD-7545 or the like are illustrated; as hepatic gluconeogenesis inhibitors, FR-225659 or the like are illustrated; as glucagon-like peptide-1 analogues, exendin-4, CJC-1131 or the like are illustrated; as glucagon-like peptide 1 agonists; AZM-134, LY-315902 or the like are illustrated; and as amylin, amylin analogues or amylin agonists, pramlintide acetate or the like are illustrated. These drugs, glucose-6-phosphatase inhibitors, D-chiroinsitol, glycogen synthase kinase-3 inhibitors and glucagon-like peptide-1 are used preferably for diabetes, impaired glucose tolerance, diabetic complications or hyperinsulinemia, and more preferably for diabetes or impaired glucose tolerance.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat or the like are illustrated. Aldose reductase inhibitors are preferably used for diabetic complications because of inhibiting aldose reductase and lowering excessive intracellular accumulation of sorbitol in accelerated polyol pathway which are in continuous hyperglycemic condition in the tissues in diabetic complications.

As advanced glycation end products formation inhibitors, pyridoxamine, OPB-9195, ALT-946, ALT-711, pimagedine hydrochloride or the like are illustrated. Advanced glycation end products formation inhibitors are preferably used for diabetic complications because of inhibiting formation of advanced glycation end products which are accelerated in continuous hyperglycemic condition in diabetes and declining of cellular damage.

As protein kinase C inhibitors, LY-333531, midostaurin or the like are illustrated. Protein kinase C inhibitors are preferably used for diabetic complications because of inhibiting of protein kinase C activity which is accelerated in continuous hyperglycemic condition in diabetes.

As γ-aminobutyric acid receptor antagonists, topiramate or the like are illustrated; as sodium channel antagonists, mexiletine hydrochloride, oxcarbazepine or the like are illustrated; as transcript factor NF-κB inhibitors, dexlipotam or the like are illustrated; as lipid peroxidase inhibitors, tirilazad mesylate or the like are illustrated; as N-acetylated-α-linked-acid-dipeptidase inhibitors, GPI-5693 or the like are illustrated; and as carnitine derivatives, carnitine, levacecarnine hydrochloride, levocarnitine chloride, levocarnitine, ST-261 or the like are illustrated. These drugs, insulin-like growth factor-I, platelet-derived growth factor, platelet derived growth factor analogues, epidermal growth factor, nerve growth factor, uridine, 5-hydroxy-1-methylhydantoin, EGB-761, bimoclomol, sulodexide and Y-128 are preferably used for diabetic complications.

As hydroxymethylglutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin or the like are illustrated. Hydroxymethylglutaryl coenzyme A reductase inhibitors are used preferably for hyperlipidemia, hypercholesterolemia, hypertriglyceridemia, lipid metabolism disorder or atherosclerosis, and more preferably for hyperlipidemia, hypercholesterolemia or atherosclerosis because of lowering blood cholesterol level by inhibiting hydroxymethylglutaryl coenzyme A reductase.

As fibric acid derivatives, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 or the like are illustrated. Fibric acid derivatives are used preferably for hyperinsulinemia, hyperlipidemia, hypercholesterolemia, hypertriglyceridemia, lipid metabolism disorder or atherosclerosis, and more preferably for hyperlipidemia, hypertriglyceridemia or atherosclerosis because of activating hepatic lipoprotein lipase and enhancing fatty acid oxidation, leading to lowering of blood triglyceride level.

As $\beta_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696, YM178 or the like are illustrated. $\beta_3$-Adrenoceptor agonists are used preferably for obesity, hyperinsulinemia, hyperlipidemia, hypercholesterolemia, hypertriglyceridemia or lipid metabolism disorder, and more preferably for obesity or hyperinsulinemia because of stimulating $\beta_3$-adrenoceptor in adipose tissue and enhancing the fatty acid oxidation, leading to induction of energy expenditure.

As acyl-coenzyme A cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe or the like are illustrated. Acyl-coenzyme A cholesterol acyltransferase inhibitors are used preferably for hyperlipidemia, hypercholesterolemia, hypertriglyceridemia or lipid metabolism disorder, and more preferably for hyperlipidemia or hypercholesterolemia because of lowering blood cholesterol level by inhibiting acyl-coenzyme A cholesterol acyltransferase.

As thyroid hormone receptor agonists, sodium liothyronine, sodium levothyroxine, KB-2611 or the like are illustrated; as cholesterol absorption inhibitors, ezetimibe, SCH-48461 or the like are illustrated; as lipase inhibitors, orlistat, ATL-962, AZM-131, RED-103004 or the like are illustrated; as carnitine palmitoyltransferase inhibitors, etomoxir or the like are illustrated; as squalene synthase inhibitors, SDZ-268-198, BMS-188494, A-87049, RPR-101821, ZD-9720, RPR-107393, ER-27856 or the like are illustrated; as nicotinic acid derivatives, nicotinic acid, nicotinamide, nicomol, niceritrol, acipimox, nicorandil or the like are illustrated; as bile acid sequestrants, colestyramine, colestilan, colesevelam hydrochloride, GT-102-279 or the like are illustrated; as sodium/bile acid cotransporter inhibitors, 264W94, S-8921, SD-5613 or the like are illustrated; and as cholesterol ester transfer protein inhibitors, PNU-107368E, SC-795, JTT-705, CP-529414 or the like are illustrated. These drugs, probcol, microsomal triglyceride transfer protein inhibitors, lipoxygenase inhibitors and low-density lipoprotein receptor enhancers are preferably used for hyperlipidemia, hypercholesterolemia, hypertriglyceridemia or lipid metabolism disorder.

As appetite suppressants, monoamine reuptake inhibitors, serotonin reuptake inhibitors, serotonin releasing stimulants, serotonin agonists (especially $5HT_{2C}$-agonists), noradrenaline reuptake inhibitors, noradrenaline releasing stimulants, $\alpha_1$-adrenoceptor agonists, $\beta_2$-adrenoceptor agonists, dopamine agonists, cannabinoid receptor antagonists, $\gamma$-aminobutyric acid receptor antagonists, $H_3$-histamine antagonists, L-histidine, leptin, leptin analogues, leptin receptor agonists, melanocortin receptor agonists (especially, MC3-R agonists, MC4-R agonists), $\alpha$-melanocyte stimulating hormone, cocaine-and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotrophin-releasing hormone analogues, corticotropin-releasing hormone agonists, urocortin, somatostatin, somatostatin analogues, somatostatin receptor agonists, pituitary adenylate cyclase-activating peptide, brain-derived neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone antagonists, agouti-related protein inhibitors and orexin receptor antagonists are illustrated. Concretely, as monoamine reuptake inhibitors, mazindol or the like are illustrated; as serotonin reuptake inhibitors, dexfenfluramine hydrochloride, fenfluramine, sibutramine hydrochloride, fluvoxamine maleate, sertraline hydrochloride or the like are illustrated; as serotonin agonists, inotriptan, (+)-norfenfluramine or the like are illustrated; as noradrenaline reuptake inhibitors, bupropion, GW-320659 or the like are illustrated; as noradrenaline releasing stimulants, rolipram, YM-992 or the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex or the like are illustrated; as dopamine agonists, ER-230, doprexin, bromocriptine mesylate or the like are illustrated; as cannabinoid receptor antagonists, rimonabant or the like are illustrated; as $\gamma$-aminobutyric acid receptor antagonists, topiramate or the like are illustrated; as $H_3$-histamine antagonists, GT-2394 or the like are illustrated; as leptin, leptin analogues or leptin receptor agonists, LY-355101 or the like are illustrated; as cholecystokinin agonists (especially CCK-A agonists), SR-146131, SSR-125180, BP-3.200, A-71623, FPL-15849, GI-248573, GW-7178, GI-181771, GW-7854, A-71378 or the like are illustrated; and as neuropeptide Y antagonists, SR-120819-A, PD-160170, NGD-95-1, BIBP-3226, 1229-U-91, CGP-71683, BIBO-3304, CP-671906-01, J-115814 or the like are illustrated. Appetite suppressants are used preferably for diabetes, impaired glucose tolerance, diabetic complications, obesity, hyperlipidemia, hypercholesterolemia, hypertriglyceridemia, lipid metabolism disorder, atherosclerosis, hypertension, congestive heart failure, edema, hyperuricemia or gout, and more preferably for obesity because of stimulating or inhibiting the activities of intracerebral monoamines or bioactive peptides in central appetite regulatory system and suppressing the appetite, leading to reduction of energy intake.

As angiotensin-converting enzyme inhibitors, captopril, enalapril maleate, alacepril, delapril hydrochloride, ramipril, lisinopril, imidapril hydrochloride, benazepril hydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril or the like are illustrated. Angiotensin-converting enzyme inhibitors are preferably used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril or the like are illustrated. Neutral endopeptidase inhibitors are preferably used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 or the like are illustrated. Angiotensin II receptor antagonists are preferably used for diabetic complications or hypertension.

As endothelin-converting enzyme inhibitors, CGS-31447, CGS-35066, SM-19712 or the like are illustrated; as endothelin receptor antagonists, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 or the like are illustrated. These drugs are preferably used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-α, PNU-80873A, isosorbide, D-mannitol, D-sorbitol, fructose, glycerin, acetazolamide, methazolamide, FR-179544, OPC-31260, lixivaptan, conivaptan hydrochloride or the like are illustrated. Diuretic drugs are preferably used for diabetic complications, hypertension, congestive heart failure or edema, and more preferably for hypertension, congestive heart failure or edema because of reducing blood pressure or improving edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride or the like are illustrated; as vasodilating antihypertensive agents, indapamide, todralazine hydrochloride, hydralazine hydrochloride, cadralazine, budralazine or the like are illustrated; as sympathetic blocking agents, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin or the like are illustrated; as centrally acting antihypertensive agents, reserpine or the like are illustrated; and as α$_2$-adrenoceptor agonists, clonidine hydrochloride, methyldopa, CHF-1035, guanabenz acetate, guanfacine hydrochloride, moxonidine, lofexidine, talipexole hydrochloride or the like are illustrated. These drugs are preferably used for hypertension.

As antiplatelets agents, ticlopidine hydrochloride, dipyridamole, cilostazol, ethyl icosapentate, sarpogrelate hydrochloride, dilazep dihydrochloride, trapidil, beraprost sodium, aspirin or the like are illustrated. Antiplatelets agents are preferably used for atherosclerosis or congestive heart failure.

As uric acid synthesis inhibitors, allopurinol, oxypurinol or the like are illustrated; as uricosuric agents, benzbromarone, probenecid or the like are illustrated; and as urinary alkalinizers, sodium hydrogen carbonate, potassium citrate, sodium citrate or the like are illustrated. These drugs are preferably used for hyperuricemia or gout.

In case of uses in combination with other drugs, for example, in the use for diabetic complications, the combination with at least one drug of the group consisting of an insulin sensitivity enhancer, a glucose absorption inhibitor, a biguanide, aninsulin secretion enhancer, a SGLT inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, glycogen synthase kinase-3 inhibitors, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhydantoin, EGB-761, bimoclomol, sulodexide, Y-128, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the combination with at least one drug of the group consisting of an aldose reductase inhibitor, an angiotensin-converting enzyme inhibitor, a neutral endopeptidase inhibitor and an angiotensin II receptor antagonist is more preferable. Similarly, in the use for diabetes, the combination with at least one drug of the group consisting of an insulin sensitivity enhancer, a glucose absorption inhibitor, a biguanide, an insulin secretion enhancer, a SGLT2 inhibitors, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist and an appetite suppressant is preferable; the combination with at least one drug of the group consisting of an insulin sensitivity enhancer, a biguanide, an insulin secretion enhancer, a SGLT2 inhibitors, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue and an amylin agonist is more preferable; and the combination with at least one drug of the group consisting of an insulin sensitivity enhancer, a biguanide, an insulin secretion enhancer, a SGLT2 inhibitor and an insulin or insulin analogue is most preferable. Furthermore, in the use for obesity, the combination with at least one drug of the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $\beta_3$-adrenoceptor agonist and an appetite suppressant is preferable; and the combination with at least one drug of the group consisting of a SGLT2 inhibitor, a $\beta_3$-adrenoceptor agonist and an appetite suppressant is more preferable.

When the pharmaceutical compositions of the present invention are employed in the practical treatment, various dosage forms are used depending on their uses. As examples of the dosage forms, powders, granules, fine granules, dry syrups, tablets, capsules, topical dosages (e.g., transdermal absorption preparations), injections, suppositories, solutions and the like are illustrated, which are orally or parenterally administered. The pharmaceutical compositions of the present invention can also include sustained release formulation and enteric coated preparation.

These pharmaceutical compositions can be prepared optionally by admixing, diluting, dissolving and then coating using an appropriate pharmaceutical additive such as excipients, disintegrators, binders, lubricants, diluents, buffers, isotonicities, antiseptics, moistening agents, emulsifiers, dispersing agents, stabilizing agents, dissolving aids, viscosity-increasing agents, gelling agents, hardening agents, absorbents, viscosing agents, elasticating agents, plasticizers, coating agents, sustained-releasing agent, antioxidants, light shielding agents, antistatic agents, fragrances, sweetening agents, flavors, coloring agents, soothing agents and the like, and formulating the mixture in accordance with conventional methods. In case of the uses of the compound of the present invention in combination with other drug(s), they can be prepared by formulating each active ingredient together or individually.

When the pharmaceutical compositions of the present invention are employed in the practical treatment, the dosage of a compound represented by the above general formula (I), or a pharmaceutically acceptable salt thereof or a prodrug thereof as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably. Also, in case of the uses of the compound of the present invention in combination with the other drug(s), the dosage of the compound of the present invention can be decreased, depending on the dosage of the other drug(s).

BEST MODE FOR CARRYING OUT THE INVENTION

Figure 1:
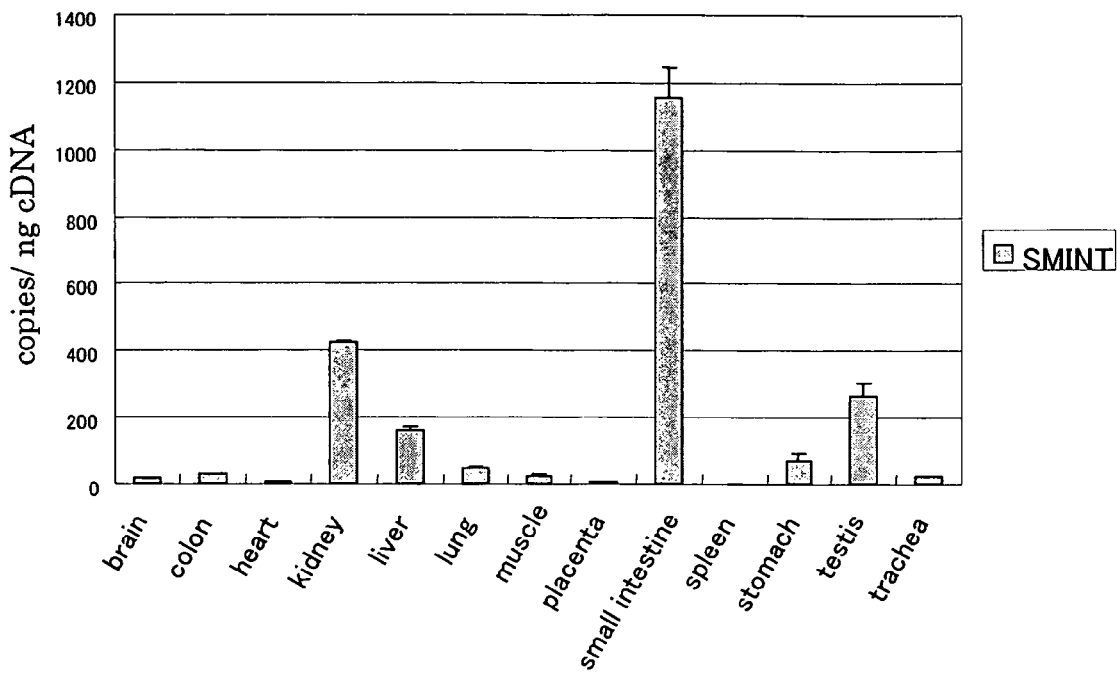
FIG. 1 is a graph showing the distribution pattern of SMINT gene expression among human organs. The vertical axis indicates copy number/ng cDNA, and the horizontal axis indicates the name of human organ.

The present invention is further illustrated in more detail by way of the following Reference Examples, Examples and Test Examples. However, the present invention is not limited thereto.

REFERENCE EXAMPLE 1

Ethyl 3-hydroxy-1-isopropylpyrazole-4-carboxylate

To a solution of sodium methoxide (23 g) in ethanol (150 mL) were added diethyl ethoxymethylene malonate (32.7 g) and isopropyl hydrazine (11.2 g) at room temperature. The mixture was stirred at 80° C. for 4 hours and stirred at 100° C. for another 2 hours. The reaction mixture was poured into 2 mol/L hydrochloric acid (300 mL). After the mixture was diluted with brine, the mixture was extracted with ethyl acetate. The organic layer was washed with brine and dried over anhydrous magnesium sulfate. The solvent was removed under reduced pressure and the obtained residue was purified by column chromatography on silica gel (eluent: ethyl acetate/hexane=1/5) to give 10.5 g of the title compound.

$^1$H-NMR (CDCl$_3$) $\delta$ ppm: 1.35 (3H, t, J=7.0 Hz), 1.48 (6H, d, J=6.7 Hz), 4.20-4.40 (3H, m), 7.60 (1H, s)

REFERENCE EXAMPLE 2

Ethyl 5-bromo-3-hydroxy-1-isopropylpyrazole-4-carboxylate

Ethyl 3-hydroxy-1-isopropylpyrazole-4-carboxylate (10.5 g) was dissolved in dichloromethane (100 mL) and to the stirred solution was added N-bromosuccinimide (14.1 g) under ice cooling. The reaction mixture was stirred at room temperature for 6 hours. The solvent was removed under reduced pressure and the obtained residue was purified by column chromatography on silica gel (eluent: ethyl acetate/hexane=1/5) to give 5.9 g of the title compound.

$^1$H-NMR (CDCl$_3$) $\delta$ ppm: 1.39 (3H, t, J=7.0 Hz), 1.44 (6H, d, J=6.6 Hz), 4.37 (2H, q, J=7.0 Hz), 4.60-4.80 (1H, m), 8.34 (1H, s)

REFERENCE EXAMPLE 3

Ethyl 3-benzyloxy-5-bromo-1-isopropylpyrazole-4-carboxylate

Ethyl 5-bromo-3-hydroxy-1-isopropylpyrazole-4-carboxylate (5.8 g) and potassium carbonate (3.5 g) were suspended in N,N-dimethylformamide (50 mL) and to the stirred suspension was added benzyl bromide (2.76 mL) under ice cooling. The mixture was stirred at room temperature for 6 hours. The reaction mixture was poured into 1 mol/L hydrochloric acid (100 mL) and the mixture was extracted with ethyl acetate. The organic layer was washed with brine and dried over anhydrous magnesium sulfate. The solvent was removed under reduced pressure and the obtained residue was purified by column chromatography on silica gel (eluent: ethyl acetate/hexane=1/5) to give 7.7 g of the title compound.

$^1$H-NMR (CDCl$_3$) δ ppm: 1.35 (3H, t, J=7.1 Hz), 1.42 (6H, d, J=6.6 Hz), 4.30 (2H, q, J=7.1 Hz), 4.60-4.80 (1H, m), 5.32 (2H, s), 7.20-7.60 (5H, m)

REFERENCE EXAMPLE 4

3-Benzyloxy-5-bromo-1-isopropylpyrazole-4-carboxylic acid

Ethyl 3-benzyloxy-5-bromo-1-isopropylpyrazole-4-carboxylate (7.7 g) was suspended in 1,4-dioxane (19 mL) and 20% sodium hydroxide aqueous solution (19 mL) was added to the suspension. The mixture was stirred at 100° C. for 8 hours. After the reaction mixture was cooled, the reaction mixture was poured into 2 mol/L hydrochloric acid (100 mL) and the mixture was extracted with ethyl acetate. The organic layer was washed with brine and dried over anhydrous magnesium sulfate. The solvent was removed under reduced pressure to give 4.6 g of the title compound.
$^1$H-NMR (CDCl$_3$) δ ppm: 1.43 (6H, d, J=6.7 Hz), 4.60-4.85 (1H, m), 5.34 (2H, s), 7.20-7.65 (5H, m)

REFERENCE EXAMPLE 5

3-Benzyloxy-5-bromo-4-hydroxymethyl-1-isopropyl-1H-pyrazole

3-Benzyloxy-5-bromo-1-isopropylpyrazole-4-carboxylic acid (4.6 g) was dissolved in tetrahydrofuran (30 mL) and to the stirred solution was added dropwise 1M solution of borane-tetrahydrofuran complex in tetrahydrofuran (21 mL) under ice cooling. The mixture was stirred at room temperature for 1 hour. The reaction mixture was cooled with ice bath and to the reaction mixture was dropwise added 50 mL of water. Then 1 mol/L hydrochloric acid (20 mL) was added dropwise to the mixture and the mixture was extracted with ethyl acetate. The organic layer was washed with brine and dried over anhydrous magnesium sulfate. The solvent was removed under reduced pressure and the obtained residue was purified by column chromatography on silica gel (eluent: ethyl acetate/hexane=1/5) to give 3.0 g of the title compound.
$^1$H-NMR (CDCl$_3$) δ ppm: 1.41 (6H, d, J=6.6 Hz), 1.51 (1H, t, J=6.1 Hz), 4.43 (2H, d, J=6.1 Hz), 4.50-4.68 (1H, m), 5.25 (2H, s), 7.20-7.60 (5H, m)

REFERENCE EXAMPLE 6

3-Benzyloxy-5-bromo-4-fomyl-1-isopropyl-1H-pyrazole

3-Benzyloxy-5-bromo-4-hydroxymethyl-1-isopropyl-1H-pyrazole (3.0 g) was dissolved in dichloromethane (30 mL) and manganese dioxide (4 g) was added to the stirred solution at room temperature. The reaction mixture was stirred at 50° C. for 1 hour. The insoluble material was removed by filtration and the filtrate was concentrated under reduced pressure to give 2.7 g of the title compound.
$^1$H-NMR (CDCl$_3$) δ ppm: 1.44 (6H, d, J=6.7 Hz), 4.55-4.75 (1H, m), 5.34 (2H, s), 7.20-7.60 (5H, m), 9.75 (1H, s)

REFERENCE EXAMPLE 7

3-Benzyloxy-5-bromo-4-[hydroxy(4-methoxyphenyl)methyl]-1-isopropyl-1H-pyrazole

3-Benzyloxy-5-bromo-4-fomyl-1-isopropyl-1H-pyrazole (0.7 g) was dissolved in tetrahydrofuran (5 mL). To the stirred solution was added a solution of 4-methoxyphenylmagnesium bromide in tetrahydrofuran (0. 5 mL/L, 4. 3 mL) at room temperature and the mixture was stirred at room temperature for 1 hour. A small amount of a saturated ammonium chloride aqueous solution was added to the reaction mixture and the mixture was purified by column chromatography on aminopropylated silica gel (eluent: tetrahydrofuran) to give 0.6 g of the title compound.
$^1$H-NMR (CDCl$_3$) δ ppm: 1.40 (6H, d, J=6.6 Hz), 2.65 (1H, d, J=7.5 Hz), 3.79 (3H, s), 4.45-4.65 (1H, m), 5.15-5.35 (2H, m), 5.66 (1H, d, J=7.5 Hz), 6.83 (2H, d, J=9.0 Hz), 7.20-7.45 (7H, m)

REFERENCE EXAMPLE 8

3-Benzyloxy-5-bromo-4-[hydroxyl(2,4-dimethoxyphenyl)methyl]-1-isopropyl-1H-pyrazole The title compound was prepared in a similar manner to that described in Reference Example 7 using a corresponding starting material.
$^1$H-NMR (CDCl$_3$) δ ppm: 1.39 (3H, d, J=6.5 Hz), 1.40 (3H, d, J=6.7 Hz), 3.05 (1H, d, J=6.6 Hz), 3.76 (3H, s), 3.79 (3H, s), 4.45-4.65 (1H, m), 5.15-5.35 (2H, m), 5.91 (1H, d, J=6.6 Hz), 6.40 (1H, dd, J=2.3 Hz, 8.6 Hz), 6.42 (1H, d, J=2.3 Hz), 7.15-7.45 (6H, m)

REFERENCE EXAMPLE 9

3-Benzyloxy-5-bromo-1-isopropyl-4-(4-methoxybenzoyl)-1H-pyrazole

3-Benzyloxy-5-bromo-4-[hydroxyl(4-methoxyphenyl)methyl]-1-isopropyl-1H-pyrazole (0.6 g) was dissolved in dichloromethane (10 mL). To the stirred solution was added Manganese dioxide (0.5 g) at room temperature and the mixture was stirred at 50° C. for 1 hour. After the insoluble material was removed by filtration, the filtrate was concentrated under reduced pressure to give the title compound (0.4 g).
$^1$H-NMR (CDCl$_3$) δ ppm: 1.47 (6H, d, J=6.6 Hz), 3.86 (3H, s), 4.60-4.80 (1H, m), 5.23 (2H, s), 6.87 (2H, d, J=8.9 Hz), 7.15-7.40 (5H, m), 7.81 (2H, d, J=8.9 Hz)

REFERENCE EXAMPLE 10

3-Benzyloxy-5-bromo-1-isopropyl-4-(2,4-diemthoxybenzoyl)-1H-pyrazole

The title compound was prepared in a similar manner to that described in Reference Example 9 using a corresponding starting material.
$^1$H-NMR (CDCl$_3$) δ ppm: 1.45 (6H, d, J=6.6 Hz), 3.61 (3H, s), 3.83 (3H, s), 4.65-4.85 (1H, m), 5.15 (2H, s), 6.33 (1H, d, J=2.3 Hz), 6.49 (1H, dd, J=2.3 Hz, 8.6 Hz), 7.00-7.15 (2H, m), 7.18-7.30 (3H, m), 7.38 (1H, d, J=8.6 Hz)

REFERENCE EXAMPLE 11

3-Benzyloxy-1-isopropyl-4-(4-methoxybenzoyl)-5-phenoxy-1H-pyrazole

3-Benzyloxy-5-bromo-1-isopropyl-4-(4-methoxybenzoyl)-1H-pyrazole (43 mg), phenol (14 mg) and potassium carbonate (21 mg) were suspended in N,N-dimethylacetoamide (5 mL) and the mixture was stirred under reflux for 2 hours. The mixture was allowed to cool to room temperature, then 10% citric acid aqueous solution was added to the reaction mixture and the mixture was extracted with ethyl acetate. The organic layer was sequentially washed with a saturated sodium hydrogen carbonate and brine. After the solution was dried over anhydrous magnesium sulfate, the solvent was removed under reduced pressure. The obtained residue was purified by column chromatography on silica gel (eluent: hexane/ethyl acetate=5/1) to give the title compound, (24 mg).
$^1$H-NMR (CDCl$_3$) δ ppm: 1.42 (6H, d, J=6.6 Hz), 3.82 (3H, s), 4.40-4.55 (1H, m), 5.31 (2H, s), 6.79 (2H, d, J=8.8 Hz), 6.82 (2H, d, J=7.9 Hz), 6.99 (1H, t, J=7.4 Hz), 7.10-7.45 (7H, m), 7.67 (2H, d, J=8.8 Hz)

REFERENCE EXAMPLE 12

3-Benzyloxy-4-(2,4-dimethoxybenzoyl)-1-isopropyl-5-(4-methoxyphenoxy)-1H-pyrazole The title compound was prepared in a similar manner to that described in Reference Example 11 using a corresponding starting material.
$^1$H-NMR (CDCl$_3$) δ ppm: 1.40 (6H, d, J=6.5 Hz), 3.58 (3H, s), 3.73 (3H, s), 3.79 (3H, s), 4.35-4.55 (1H, m), 5.25 (2H, s), 6.25 (1H, d, J=2.3 Hz), 6.37 (1H, dd, J=2.3 Hz, 8.5 Hz), 6.66-6.85 (4H, m), 7.10-7.38 (6H, m)

REFERENCE EXAMPLE 13

3-Benzyloxy-4-(2,4-dimethoxybenzoyl)-1-isopropyl-5-piperidino-1H-pyrazole

The title compound was prepared in a similar manner to that described in Reference Example 11 using a corresponding starting material.
$^1$H-NMR (CDCl$_3$) δ ppm: 1.40 (6H, d, J=6.5 Hz), 1.45-1.75 (6H, m), 2.95-3.25 (4H, m), 3.64 (3H, s), 3.83 (3H, s), 4.65-4.88 (1H, m), 5.08 (2H, s), 6.35 (1H, d, J=2.3 Hz), 6.45 (1H, dd, J=2.3 Hz, 8.4 Hz), 6.85-7.00 (2H, m), 7.10-7.30 (3H, m), 7.38 (1H, d, J=8.4 Hz)

REFERENCE EXAMPLE 14

3-Benzyloxy-4-(2,4-dimethoxybenzoyl)-1-isopropyl-5-pyrazolyl-1H-pyrazole

The title compound was prepared in a similar manner to that described in Reference Example 11 using a corresponding starting material.
$^1$H-NMR (CDCl$_3$) δ ppm: 1.42 (6H, d, J=6.6 Hz), 3.62 (3H, s), 3.80 (3H, s), 4.20-4.45 (1H, m), 5.26 (2H, s), 6.26 (1H, d, J=2.2 Hz), 6.33 (1H, dd, J=1.7 Hz, 2.5 Hz), 6.39 (1H, dd, J=2.2 Hz, 8.5 Hz), 7.10-7.30 (5H, m), 7.33 (1H, d, J=8.5 Hz), 7.70 (1H, d, J=1.7 Hz), 7.77 (1H, d, J=2.5 Hz)

REFERENCE EXAMPLE 15

1-Isopropyl-4-(4-methoxybenzyl)-5-phenoxy-1,2-dihydro-3H-pyrazol-3-one

Sodium borohydride (10 mg) was suspended in tetrahydrofuran (1 mL) and to the stirred suspension was added dropwise a solution of 3-benzyloxy-1-isopropyl-4-(4-methoxybenzoyl)-5-phenoxy-1H-pyrazole (24 mg) in tetrahydrofuran (4 mL) under ice cooling. The mixture was stirred at room temperature for 3 hours and 1 mL of 10% citric acid aqueous solution was added dropwise to the reaction mixture, and the mixture was extracted with ethyl acetate. The organic layer was sequentially washed with a saturated sodium hydrogen carbonate and brine. After the solution was dried over anhydrous magnesium sulfate, the solvent was removed under reduced pressure and the obtained residue was dissolved in ethanol (5 mL). To the stirred solution was added 10% palladium carbon powder under ice cooling and the suspension was stirred at room temperature for 6 hours under hydrogen atmosphere at normal pressure. Insoluble material was removed by filtration and the solvent of filtrate was removed under reduced pressure to give the title compound (10 mg).
$^1$H-NMR (CDCl$_3$) δ ppm: 1.35 (6H, d, J=6.8 Hz), 3.42 (2H, s), 3.74 (3H, s), 4.20-4.40 (1H, m), 6.69 (2H, d, J=8.5 Hz), 6.85 (2H, d, J=7.5 Hz), 7.00 (2H, d, J=8.5 Hz), 7.05 (1H, t, J=7.5 Hz), 7.15-7.40 (2H, m)

REFERENCE EXAMPLE 16

1-Isopropyl-4-(2,4-dimethoxybenzyl)-5-(4-methoxyphenoxy)-1,2-dihydro-3H-pyrazol-3-one The title compound was prepared in a similar manner to that described in Reference Example 15 using a corresponding starting material.
$^1$H-NMR (CDCl$_3$) δ ppm: 1.31 (6H, d, J=7.0 Hz), 3.39 (2H, s), 3.75 (3H, s), 3.77 (3H, s), 3.78 (3H, s), 4.15-4.35 (1H, m), 6.30 (1H, dd, J=2.6 Hz, 8.1 Hz), 6.38 (1H, d, J=2.6 Hz), 6.70-6.90 (5H, m)

REFERENCE EXAMPLE 17

1-Isopropyl-4-(2,4-dimethoxybenzyl)-5-piperidino-1,2-dihydro-3H-pyrazol-3-one

The title compound was prepared in a similar manner to that described in Reference Example 15 using corresponding starting material.
$^1$H-NMR (CDCl$_3$) δ ppm: 1.26 (6H, d, J=6.6 Hz), 1.30-1.90 (6H, m), 2.88-3.10 (4H, m), 3.63 (2H, s), 3.77 (3H, s), 3.85 (3H, s), 4.15-4.40 (1H, m), 6.40 (1H, dd, J=2.6 Hz, 8.4 Hz), 6.44 (1H, d, J=2.6 Hz), 7.01 (1H, d, J=8.4 Hz)

REFERENCE EXAMPLE 18

1-Isopropyl-4-(2,4-dimethoxybenzyl)-5-pyrazolyl-1,2-dihydro-3H-pyrazol-3-one

The title compound was prepared in a similar manner to that described in Reference Example 15 using a corresponding starting material.
$^1$H-NMR (CDCl$_3$) δ ppm: 1.35 (6H, d, J=6.5 Hz), 3.47 (2H, s), 3.76 (3H, s), 3.82 (3H, s), 3.90-4.10 (1H, m), 6.39 (1H, dd, J=2.4 Hz, 8.5 Hz), 6.42 (1H, d, J=2.4 Hz), 6.43 (1H, dd, J=1.7 Hz, 2.2 Hz), 6.87 (1H, d, J=8.5 Hz), 7.46 (1H, d, J=2.2 Hz), 7.79 (1H, d, J=1.7 Hz)

EXAMPLE 1

1-Isopropyl-4-(4-methoxybenzyl)-5-phenoxy-3-(β-D-glucopyranosyloxy)-1H-pyrazole

To a suspension of 1-isopropyl-4-(4-methoxybenzyl)-5-phenoxy-1,2-dihydro-3H-pyrazol-3-one (10 mg), acetobromo-α-D-glucose (40 mg) and benzyl(n-tributyl)ammonium chloride (30 mg) in dichloromethane (3 mL) was added sodium hydroxide aqueous solution (2 mol/L, 0.1 mL) and the mixture was stirred at room temperature for 2 hours. The reaction mixture was purified by column chromatography on aminopropylated silica gel (eluent: tetrahydrofuran). The obtained semi-purified 1-isopropyl-4-(4-methoxybenzyl)-5-phenoxy-3-(2,3,4,6-tetra-O-acetyl-β-D-glucopyranosyloxy-1H-pyrazole was dissolved in methanol (5 mL) and sodium methoxide (28% methanol solution, 0.2 mL) was added to the solution. The mixture was stirred at room temperature for 2 hours. The reaction mixture was concentrated under reduced pressure and to the residue was added 10% citric acid aqueous solution. The mixture was extracted with ethyl acetate. The organic layer was washed with brine, dried over anhydrous magnesium sulfate and the solvent was removed under reduced pressure. The obtained residue was purified by preparative reverse phase column chromatography (Shiseido CAPSELLPAC C18 UG80, 5 μm, 20×50 mm, flowrate 30 mL/min linear gradient, water/methanol=70/30-10/90) to give 10 mg of the title compound.

$^1$H-NMR (CD$_3$OD) δ ppm: 1.15-1.45 (6H, m), 3.10-3.60 (6H, m), 3.63-3.77 (4H, m), 3.85 (1H, dd, J=1.8 Hz, 12.0 Hz), 4.23-4.45 (1H, m), 5.25 (1H, d, J=7.4 Hz), 6.66 (2H, d, J=8.4 Hz), 6.79 (2H, d, J=8.8 Hz), 6.93 (2H, d, J=8.4 Hz), 7.05 (1H, t, J=7.5 Hz), 7.25 (2H, dd, J=7.5 Hz, 8.8 Hz)

EXAMPLE 2

1-Isopropyl-4-(2,4-dimethoxyphenylmethyl)-5-(4-methoxyphenyloxy)-3-(β-D-glucopyranosyloxy)-1H-pyrazole The title compound was prepared in a similar manner to that described in Example 1 using a corresponding starting material.

$^1$H-NMR (CD$_3$OD) δ ppm: 1.25-1.40 (6H, m), 3.25-3.50 (6H, m), 3.60 (3H, s), 3.69 (1H, dd, J=5.4 Hz, 12.2 Hz), 3.715 (3H, s), 3.723 (3H, s), 3.83 (1H, dd, J=2.4 Hz, 12.2 Hz), 4.25-4.45 (1H, m), 5.21 (1H, d, J=7.6 Hz), 6.25-6.35 (2H, m), 6.65 (2H, d, J=9.1 Hz), 6.73 (2H, d, J=9.1 Hz), 6.88 (1H, d, J=6.9 Hz)

EXAMPLE 3

1-Isopropyl-4-(2,4-dimethoxyphenylmethyl)-5-piperidino-3-(β-D-glucopyranosyloxy)-1H-pyrazole The title compound was prepared in a similar manner to that described in Example 1 using a corresponding starting material.

$^1$H-NMR (CD$_3$OD) δ ppm: 1.34 (3H, d, J=6.7 Hz), 1.35 (3H, d, J=6.6 Hz), 1.38-1.63 (6H, m), 2.70-2.90 (4H, m), 3.10-3.45 (4H, m), 3.64 (1H, dd, J=5.0 Hz, 12.0 Hz), 3.71 (2H, s), 3.72-3.79 (4H, m), 3.84 (3H, s), 4.60-4.80 (1H, m), 5.02 (1H, d, J=7.4 Hz), 6.38 (1H, dd, J=2.3 Hz, 8.6 Hz), 6.50 (1H, d, J=2.3 Hz), 6.82 (1H, d, J=8.6 Hz)

EXAMPLE 4

1-Isopropyl-4-(2,4-dimethoxyphenylmethyl)-5-(1H-pyrazol-1-yl)-3-(β-D-glucopyranosyloxy)-1H-pyrazole The title compound was prepared in a similar manner to that described in Example 1 using corresponding a starting material.

$^1$H-NMR (CD$_3$OD) δ ppm: 1.32 (3H, d, J=6.6 Hz), 1.33 (3H, d, J=6.6 Hz), 3.20-3.50 (4H, m), 3.55 (2H, s), 3.65 (3H, s), 3.69 (1H, dd, J=5.1 Hz, 12.1 Hz), 3.72 (3H, s), 3.82 (1H, dd, J=2.3 Hz, 12.1 Hz), 3.90-4.03 (1H, m), 5.27 (1H, d, J=7.5 Hz), 6.33 (1H, dd, J=2.3 Hz, 8.5 Hz), 6.36 (1H, d, J=2.3 Hz), 6.45 (1H, dd, J=1.9 Hz, 2.4 Hz), 6.89 (1H, d, J=8.5 Hz), 7.54 (1H, d, J=2.4 Hz), 7.73 (1H, d, J=1.9 Hz)

TEST EXAMPLE 1

Distribution Pattern of SMINT Gene Expression Among Human Organs 1) cDNA Synthesis Total RNA (tRNA) from human liver, colon, testis, pancreas, lung, small intestine, stomach, placenta and skeletal muscle were obtained from Sawady Technology, and tRNA from the trachea, brain, kidney and heart were purchased from CLONTECH. Concentrations of these tRNAs were determined by using RiboGreen RNA quantification reagent and kit (Molecular Probes), and then tRNA were proceeded to cDNA synsthesis (i.e. reverse-transcription reaction). Reaction mixture at a volume of 16.5 μL, which included 1.5 μg of tRNA and 1.5 μL of 500 ng/μL random hexamer (Invitrogen), was incubated at 70° C. for 5 minutes, then kept at room temperature for 5 minutes. After the incubation, to the above reaction mixture was added 13.5 μL of another reaction mixture containing 6 μL of 5×BRL 1$^{st}$ strand buffer (Invitrogen), 3.25 μL of distilled water (Nippon Gene), 1.5 μL of 10 mM dNTP mix (Invitrogen), 0.75 μL of RNase inhibitor (Invitrogen) and 2 μL of SuperScript II (Invitrogen). Simultaneously, another reaction mixture added 2 μL of distilled water (Nippon Gene) instead of the same volume of SuperScript II (Invitrogen) was mixed similarly with the above reaction mixture. All of the mixtures were incubated at room temperature for 10 minutes followed by the reaction at 42° C. for 1 hour. After the reaction, these mixtures were incubated at 95° C. for 10 minutes to inactivate SuperScript II (Invitrogen) immediately followed by standing on ice. Then, to the mixtures was added 1.5 μL of RNase H, and the mixture was incubated at 37° C. for 30 minutes. After the reactions, to the mixtures was added 170 μL of distilled water. The synthesized cDNA were extracted with 200 μL of phenol:chloroform:isoamylalcohol=25:24:1 (Invitrogen), and extracted again with 200 μL of chloroform:isoamylalcohol=24:1. After ethanol precipitation, the cDNA were diluted in 100 μL of distilled water (Nippon Gene).

2) Determination of SMINT Gene Expression by Real-Time Quantitative PCR

For real-time quantitative PCR, forward: 5'-TGT CAC AGT CCC CAA CAC CA-3' (SEQ ID NO. 3) and reverse: 5'-CCG AAG CAT GTG GAA AGC A-3' (SEQ ID NO. 4) as primers, and 5'-TGT CAC CTC CCA CGG CCC G-3' (SEQ ID NO. 5) as a probe were used. The probe was labeled at its 5'-end with fluorescence dye FAM, and its 3'-end with fluorescence dye TAMRA. Twenty-five μL of reaction mixture was prepared with 2.5 ng of cDNA prepared as described above, 1×Taqman Universal master mix (Applied Biosystems), 500 nM each of the forward and the reverse primers, and 200 nM of the probe. PCR condition was as follows: 1 cycle at 50° C. for 2 minutes, 1 cycle at 95° C. for 10 minutes, and 40 cycles at 95° C. for 15 seconds and at 66° C. for 1 minutes. Gene expression level was detected by GeneAmp 5700 Sequence Detection System (Applied Biosystems) in reaction tubes composed of MicroAmp optical 96-well reaction plate (Applied Biosystems) and MicroAmp optical cap (Applied Biosystems). Fluorescence signals were detected according to the manufacturer's instruction (Christian A. Heid, et al., in "Genome Research", 1996, Vol.6, pp.986-994). Serially 10-fold diluted plasmid DNA ($3.5 \times 10^6$, $3.5 \times 10^5$, $3.5 \times 10^4$, $3.5 \times 10^3$, $3.5 \times 10^2$ and $3.5 \times 10$ molecules/well, extracted from *Escherichia coli*/SMINT2010324 host cells, which is described in Test Example 2) was used to draw a standard curve for the expression analysis.

The obtained results were shown in FIG. 1. FIG. 1 indicates that human SMINT gene is expressed highly in the small intestine and the kidney. Therefore, human SMINT plays important roles in sugar absorption at the small intestine, sugar reabsorption and/or sugar uptake into the cells at the kidney.

TEST EXAMPLE 2

Confirmatory Test for Substrate Specificity of Human SMINT

1) Preparation of Cells Transiently Expressing Human SMINT

Human SMINT-carrying expression plasmid SMINT/pME18S-FL (denotation of bacteria: *Escherichia coli*/SMINT2010324), which was deposited with Patent Microorganisms Depositary at the National Institute of Technology and Evaluation under an accession number: FERMP-18756 on Mar. 12, 2002, was transfected to COS-7 cells (RIKEN CELL BANK RCB0539) by lipofection method. LIPOFECTAMINE PLUS reagent (Invitrogen) was used as the lipofection reagent. A day before the lipofection, COS-7 cells were suspended in D-MEM medium (Invitrogen) at $6 \times 10^5$ cells per 1 mL, and 50 μL of the suspended cells was dispensed into each well of 96-well plate. The lipofection was performed by the following methods. For each well, 0.1 μg of the plasmid was diluted with 10 μL of D-MEM, added 0.5 μL of PLUS reagent, mixed gently, and kept stand for 15 minutes to prepare Plasmid Dilute Solution. For each well, 0.5 μL of LIPOFECTAMINE reagent was diluted with 10 μL of D-MEM to prepare LIPOFECTAMINE Dilute Solution. The Plasmid Dilute Solution was mixed with an equal volume of the LIPOFECTAMINE Dilute Solution, kept stand for 15 minutes. After that, 20 μL of the mixture was added to each well of cell culture medium, and the cells were cultured for 5 hours at 37° C. under 5% $CO_2$. Then 100 μL of D-MEM containing 16.7% fetal bovine serum (Sanko Jun-yaku) was added to each well. After 2-day culture, the cells were used for the inhibition assay of methyl-α-D-glucopyranoside uptake activity.

2) Inhibition Assay of Methyl-α-D-glucopyranoside Uptake Activity

Figure 2:
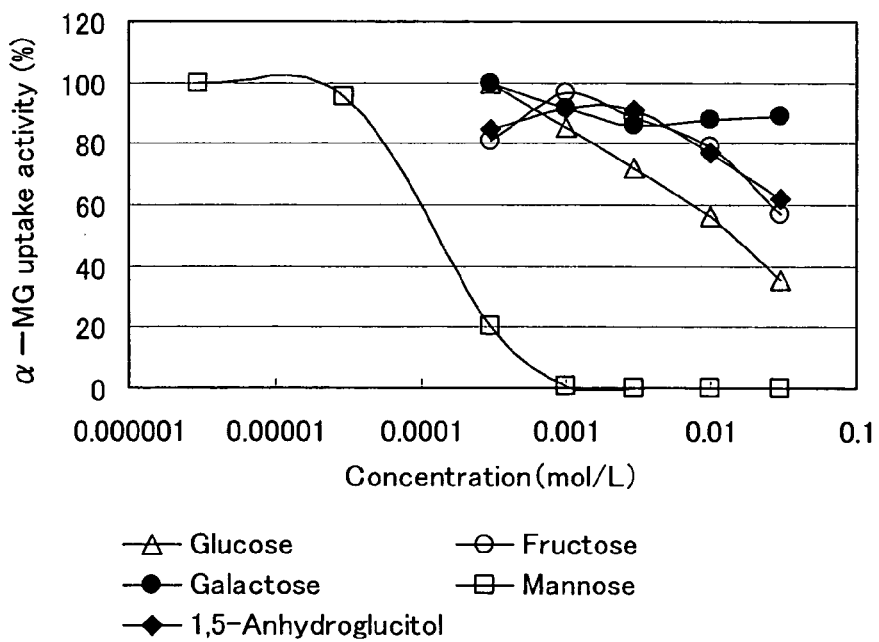
FIG. 2 is a graph showing substrate specificity of human SMINT. The vertical axis in dicates methyl-$\alpha$-D-glucopyranoside ($\alpha$-MG) uptake activity (%), and the horizontal axis indicates concentration (mol/L). In the graph, an open triangle shows glucose, an open circle shows fructose, a black circle shows galactose, an open square shows mannose and a black diamond shows 1,5-anhydroglucitol.

To Uptake Buffer consisting of 140 mM sodium chloride, 2 mM potassium chloride, 1 mM calcium chloride, 1 mM magnesium chloride, 10 mM 2-[2-(2-hydroxyethyl)-1-piperazinyl]-ethanesulfonic acid, and 5 mM tris(hydroxymethyl)aminomethane (pH 7.4), was added methyl-α-D-glucopyranoside (α-MG) composed of its non-radiolabeled form (Sigma) and $^{14}$C-labeled form (Amersham Biosciences) at 1 mM as the final concentration. For measurement of basal uptake, Basal Buffer was prepared by the addition of 140 mM choline chloride instead of sodium chloride of the Uptake Buffer. In order to determine the substrate specificity among natural sugars, natural sugars were solubilized in distilled water, diluted with distilled water into appropriate concentrations, and added to the Uptake Buffer to prepare Assay Buffer. Culture medium was discarded from the cells with transient SMINT expression, Pretreatment Buffer (Basal Buffer without α-MG) was added to the cells at 200 μL per well, and the cells were incubated at 37° C. for 10 minutes. After repeating once the same operation, Pretreatment Buffer was removed, Assay Buffer, Uptake Buffer or Basal Buffer was added to the cells at 75 μL per well, and the cells were incubated at 37° C. After the incubation for 1 hour, Assay Buffer was removed, and the cells were washed twice with 150 μL per well of Wash Buffer (Basal Buffer containing 10 mM non-radiolabeled α-MG). Cell lysates were prepared by addition of 75 μL per well of 0.2 mol/L sodium hydroxide to the cells, and transferred to PicoPlate (Packard). To the cell lysates were added 150 μL per well of MicroScint 40 (Packard), mixed well, and the radio activity was measured in a micro scintillation counter TOPCOUNT (Packard). α-MG uptake by the cells treated with each concentration of test compounds was calculated as relative activity to control group, which is set as 100% uptake after deducting the basal uptake. A concentration of a test compound inhibiting α-MG uptake by 50% ($IC_{50}$ value) was derived from logit plot analysis. The results were shown in FIG. 2. FIG. 2 indicates that SMINT recognizes 1,5-anhydroglucitol, fructose, and mannose in addition to glucose, but not galactose as substrates. Therefore, it is suggested that SMINT may be human 1,5-anhydroglucitol/fructose/mannose transporter expressed in the kidney and the other tissues.

TEST EXAMPLE 3

Confirmatory Test for Inhibitory Activity on Human SMINT

1) Preparation of Cells Transiently Expressing Human SMINT

The cells were prepared according to the method described in 1) of Test Example 2.

2) Inhibition Assay of Methyl-α-D-glucopyranoside Uptake Activity

To Uptake Buffer consisting of 140 mM sodium chloride, 2 mM potassium chloride, 1 mM calcium chloride, 1 mM magnesium chloride, 10 mM 2-[2-(2-hydroxyethyl)-1-piperazinyl]-ethanesulfonic acid, and 5 mM tris(hydroxymethyl)aminomethane (pH 7.4), was added methyl-α-D-glucopyranoside (α-MG) composed of its non-radiolabeled form (Sigma) and $^{14}$C-labeled form (Amersham Biosciences) at 1 mM as the final concentration. For measurement of basal uptake, Basal Buffer was prepared by the addition of 140 mM choline chloride instead of sodium chloride of the Uptake Buffer. Test compounds were solubilized in dimethylsulfoxide, dilited with distilled water into appropriate concentrations, and added to the Uptake Buffer to prepare Assay Buffer. Culture medium was discarded from the cells with transient SMINT expression, Pretreatment Buffer (Basal Buffer without α-MG) was added to the cells at 200 μL per well, and the cells were incubated at 37° C. for 10 minutes. After repeating once the same operation, Pretreatment Buffer was removed, Assay Buffer, Uptake Buffer or Basal Buffer was added to the cells at 75 μL per well, and the cells were incubated at 37° C. After the incubation for 1 hour, Assay Buffer was removed, and the cells were washed twice with 150 μL per well of Wash Buffer (Basal Buffer containing 10 mM non-radiolabeled α-MG). Cell lysates were prepared by addition of 75-μL per well of 0.2 mol/L sodium hydroxide to the cells, and transferred to PicoPlate (Packard). To the cell lysates were added 150 μL per well of MicroScint 40 (Packard), mixed well, and the radioactivity was measured in a microscintillation counter TOPCOUNT (Packard). α-MG uptake by the cells treated with each concentration of test compounds was calculated as relative activity to control group, which is set as 100% uptake after deducting the basal uptake. A concentration of a test compound inhibiting α-MG uptake by 50% ($IC_{50}$ value) was derived from logit plot analysis. The results were shown in Table XX. The compounds of the invention exhibited a potent inhibitory activity on SMINT. [Table 1]

TABLE 1

| Test compounds | IC50 value (nM) |
|---|---|
| Example 1 | 700 |
| Example 4 | 890 |

TEST EXAMPLE 4

Confirmatory Test for Inhibitory Activity on Human SGLT1

1) Cloning of Human SGLT1 and Transferring to Expression Vector

Total RNA from human small intestine (Ori Gene) was reverse-transcribed into cDNA for PCR amplification using oligo dT as a primer. By means of the cDNA as a template, base sequence encoding human SGLT1 reported by Hediger, et al., (Accession number: M24847, sequence from 1 to 2005) was amplified by PCR and inserted into the multicloning site of pcDNA3.1(−) vector (Invitrogen). The base sequence of inserted DNA was completely matched with the reported base sequence.

2) Preparation of Cells Transiently Expressing Human SGLT1 The above-described plasmid pcDNA3.1(−) carrying human SGLT1 DNA sequence was transfected to COS-7 cells (RIKEN CELL BANK RCB0539) by lipofection method. LIPOFECTAMINE PLUS reagent (Invitrogen) was Used as the lipofection reagent. A day before the lipofection, COS-7 cells were suspended in D-MEM medium (Invitrogen) at $6\times10^5$ cells per 1 mL, and 50 µL of the suspended cells was dispensed into each well of 96-well plate. The lipofection was performed by the following methods. For each well, 0.1 µg of the plasmid was diluted with 10 µL of D-MEM, added 0.5 µL of PLUS reagent, mixed gently, and kept stand for 15 minutes to prepare Plasmid Dilute Solution. For each well, 0.5 µL of LIPOFECTAMINE reagent was diluted with 10 µL of D-MEM to prepare LIPOFECTAMINE Dilute Solution. The Plasmid Dilute Solution was mixed with an equal volume of the LIPOFECTAMINE Dilute Solution, kept stand for 15 minutes. After that, 20 µL of the mixture was added to each well of cell culture medium, and the cells were cultured for 5 hours at 37° C. under 5% $CO_2$. Then 100 µL of D-MEM containing 16.7% fetal bovine serum (Sanko Jun-yaku) was added to each well. After 2-day culture, the cells were used for the inhibition assay of methyl-α-D-glucopyranoside uptake activity.

3) Inhibition Assay of Methyl-α-D-glucopyranoside Uptake Activity

To Uptake Buffer consisting of 140 mM sodium chloride, 2 mM potassium chloride, 1 mM calcium chloride, 1 mM magnesium chloride, 10 mM 2-[2-(2-hydroxyethyl)-1-piperazinyl]-ethanesulfonic acid, and 5 mM tris(hydroxymethyl)aminomethane (pH 7.4), was added methyl-α-D-glucopyranoside (α-MG) composed of its non-radiolabeled form (Sigma) and $^{14}C$-labeled form (Amersham Biosciences) at 1 mM as the final concentration. For measurement of basal uptake, Basal Buffer was prepared by the addition of 140 mM choline chloride instead of sodium chloride of the Uptake Buffer. Test compounds were solubilized in dimethylsulfoxide, dilited with distilled water into appropriate concentrations, and added to the Uptake Buffer to prepare Assay Buffer. Culture medium was discarded from the cells with transient human SGLT1 expression, Pretreatment Buffer (Basal Buffer without α-MG) was added to the cells at 200 µL per well, and the cells were incubated at 37° C. for 10 minutes. After repeating once the same operation, Pretreatment Buffer was removed, Assay Buffer, Uptake Buffer or Basal Buffer was added to the cells at 75 µL per well, and the cells were incubated at 37° C. After the incubation for 1 hour, Assay Buffer was removed, and the cells were washed twice with 150 µL per well of Wash Buffer (Basal Buffer containing 10 mM non-radiolabeled α-MG). Cell lysates were prepared by addition of 75 µL per well of 0.2 mol/L sodium hydroxide to the cells, and transferred to PicoPlate (Packard). To the cell lysates were added 150 µL per well of MicroScint 40 (Packard), mixed well, and the radioactivity was measured in a microscintillation counter TOPCOUNT (Packard). α-MG uptake by the cells treated with each concentration of test compounds was calculated as relative activity to control group, which is set as 100% uptake after deducting the basal uptake. A concentration of a test compound inhibiting α-MG uptake by 50% ($IC_{50}$ value) was derived from logit plot analysis.

TEST EXAMPLE 5

Confirmatory Test for Inhibitory Activity on Human SGLT2

1) Cloning of Human SGLT2 and Transferring to Expression Vector

Total RNA from human kidney (Ori Gene) was reverse-transcribed into cDNA for PCR amplification using oligo dT as a primer. By means of the cDNA as a template, base sequence encoding human SGLT2 reported by Wells, et al., (Accession number: M95549, sequence from 2 to 2039) was amplified by PCR and inserted into the multicloning site of pcDNA3.1(−) vector (Invitrogen). The base sequence of inserted DNA was completely matched with the reported sequence.

2) Preparation of Cells Transiently Expressing Human SGLT2

The above-described plasmid pcDNA3.1(−) carrying human SGLT2 DNA sequence was transfected to COS-7 cells (RIKEN CELL BANK RCB0539) by lipofection method. LIPOFECTAMINE PLUS reagent (Invitrogen) was used as the lipofection reagent. A day before the lipofection, COS-7 cells were suspended in D-MEM medium (Invitrogen) at $6\times10^5$ cells per 1 mL, and 50 µL of the suspended cells was dispensed into each well of 96-well plate. The lipofection was performed by the following methods. For each well, 0.1 µg of the plasmid was diluted with 10 µL of D-MEM, added 0.5 µL of PLUS reagent, mixed gently, and kept stand for 15 minutes to prepare Plasmid Dilute Solution. For each well, 0.5 µL of LIPOFECTAMINE reagent was diluted with 10 µL of D-MEM to prepare LIPOFECTAMINE Dilute Solution. The Plasmid Dilute Solution was mixed with an equal volume of the LIPOFECTAMINE Dilute Solution, kept stand for 15 minutes. After that, 20 µL of the mixture was added to each well of cell culture medium, and the cells were cultured for 5 hours at 37° C. under 5% $CO_2$. Then 100 µL of D-MEM containing 16.7% fetal bovine serum (Sanko Jun-yaku) was added to each well. After 2-day culture, the cells were used for the inhibition assay of methyl-α-D-glucopyranoside uptake activity.

3) Inhibition Assay of methyl-α-D-glucopyranoside Uptake Activity

To Uptake Buffer consisting of 140 mM sodium chloride, 2 mM potassium chloride, 1 mM calcium chloride, 1 mM magnesium chloride, 10 mM 2-[2-(2-hydroxyethyl)-1-piperazinyl]-ethanesulfonic acid, and 5 mM tris(hydroxymethyl)aminomethane (pH 7.4), was added methyl-α-D-glucopyranoside (α-MG) composed of its non-radiolabeled form (Sigma) and $^{14}C$-labeled form (Amersham Biosciences) at 1 mM as the final concentration. For measurement of basal uptake, Basal Buffer was prepared by the addition of 140 mM choline chloride instead of sodium chloride of the Uptake Buffer. Test compounds were solubilized in dimethylsulfoxide, dilited with distilled water into appropriate concentrations, and added to the Uptake Buffer to prepare Assay Buffer. Culture medium was discarded from the cells with transient human SGLT2 expression, Pretreatment Buffer (Basal Buffer without α-MG) was added to the cells at 200 μL per well, and the cells were incubated at 37° C. for 10 minutes. After repeating once the same operation, Pretreatment Buffer was removed, Assay Buffer, Uptake Buffer or Basal Buffer was added to the cells at 75 μL per well, and the cells were incubated at 37° C. After the incubation for 1 hour, Assay Buffer was removed, and the cells were washed twice with 150 μL per well of Wash Buffer (Basal Buffer containing 10 mM non-radiolabeled α-MG). Cell lysates were prepared by addition of 75 μL per well of 0.2 mol/L sodium hydroxide to the cells, and transferred to PicoPlate (Packard). To the cell lysates were added 150 μL per well of MicroScint 40 (Packard), mixed well, and the radioactivity was measured in a microscintillation counter TOPCOUNT (Packard). α-MG uptake by the cells treated with each concentration of test compounds was calculated as relative activity to control group, which is set as 100% uptake after deducting the basal uptake. A concentration of a test compound inhibiting α-MG uptake by 50% ($IC_{50}$ value) was derived from logit plot analysis.

INDUSTRIAL APPLICABILITY

The pyrazole derivatives represented by the above general formula (I) of the present invention, pharmaceutically acceptable salts thereof and prodrugs thereof exert a SGLT inhibitory activity and can inhibit blood glucose level increase by inhibiting the reabsorption or uptake into cells of glucose, mannose and/or fructose at the kidney or inhibiting the sugar absorption at the small intestine. Therefore, the present invention can provide an agent for the prevention, inhibition of progression or treatment of a disease associated with the excess uptake of at least a kind of carbohydrates selected from glucose, fructose and mannose such as diabetes, postprandial hyperglycemia, impaired glucose tolerance, diabetic complications or the like. In addition, since the pyrazole derivatives represented by the above general formula (II) or (III) of the present invention and salts thereof are important as intermediates in the production of the pyrazole derivatives represented by the above general formula (I), the compounds represented by the above general formula (I) of the present invention can be readily prepared via such compounds.

The invention claimed is:
1. A pyrazole derivative represented by the following general formula:

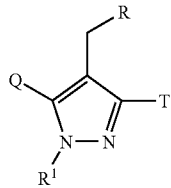

wherein
R$^1$ represents a hydrogen atom, a C$_{1-6}$ alkyl group which may have the same or different 1 to 3 groups selected from the following substituent group (A), a C$_{2-6}$ alkenyl group which may have the same or different 1 to 3 groups selected from the following substituent group (A), a C$_{2-6}$ alkynyl group which may have the same or different 1 to 3 groups selected from the following substituent group (A), a C$_{3-8}$ cycloalkyl group which may have the same or different 1 to 3 groups selected from the following substituent group (A), a C$_{6-10}$ aryl group which may have the same or different 1 to 3 groups selected from the following substituent group (B), a C$_{2-9}$ heterocycloalkyl group which may have the same or different 1 to 3 groups selected from the following substituent group (A), or a C$_{1-9}$ heteroaryl group which may have the same or different 1 to 3 groups selected from the following substituent group (B);
one of Q and T represents a group selected from

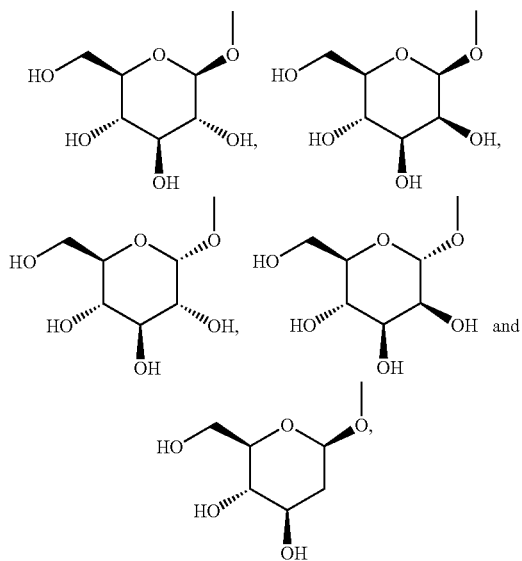

and the other represents a group represented by the formula: -Z-Ar wherein Ar represents a C$_{6-10}$ aryl group which may have the same or different 1 to 3 groups selected from the following substituent group (B) or a C$_{1-9}$ heteroaryl group which may have the same or different 1 to 3 groups selected from the following substituent group (B); and Z represents —O—, —S— or —NY— (in which Y represents a hydrogen atom or a C$_{1-6}$ alkyl group), an aliphatic cyclic amino group which may have the same or different 1 to 3 groups selected from the following substituent group (A), or an aromatic cyclic amino group which may have the same or different 1 to 3 groups selected from the following substituent group (B);
R represents a C$_{3-8}$ cycloalkyl group which may have the same or different 1 to 3 groups selected from the following substituent group (A), a C$_{6-10}$ aryl group which may have the same or different 1 to 3 groups selected from the following substituent group (B), a C$_{2-9}$ heterocycloalkyl group which may have the same or different 1 to 3 groups selected from the following substituent group (A), or a C$_{1-9}$ heteroaryl group which may have the same or different 1 to 3 groups selected from the following substituent group (B);
[Substituent Group (A)]:
a halogen atom, a nitro group, a cyano group, an oxo group, -G$^1$, —OG$^2$, —SG$^2$, —N(G$^2$)$_2$, —C(=O)G$^2$, —C(=O)OG$^2$, —C(=O)N(G$^2$)$_2$, —S(=O)$_2$G$^2$, —S(=O)$_2$OG$^2$, —S(=O)$_2$N(G$^2$)$_2$, —S(=O)G$^1$, —OC(=O)G$^1$, —OC(=O)N(G$^2$)$_2$, —NHC(=O)G$^2$, —OS(=O)$_2$G$^1$, —NHS(=O)$_2$G$^1$ and —C(=O)NHS(=O)$_2$G$^1$;
[Substituent Group (B)]:
a halogen atom, a nitro group, a cyano group, -G$^1$, —OG$^2$, —SG$^2$, —N(G$^2$)$_2$, -G$^3$OG$^4$, -G$^3$N(G$^4$)$_2$, —C(=O)G$^2$, —C(=O)OG$^2$, —C(=O)N(G$^2$)$_2$, —S(=O)$_2$G$^2$, —S(=O)$_2$OG$^2$, —S(=O)$_2$N(G$^2$)$_2$, —S(=O)G$^1$, —OC(=O)G$^1$, —OC(=O)N(G$^2$)$_2$, —NHC(=O)G$^2$, —OS(=O)$_2$G$^1$, —NHS(=O)$_2$G$^1$ and —C(=O)NHS(=O)$_2$G$^1$;
in the above substituent group (A) and/or (B),
G$^1$ represents a C$_{1-6}$ alkyl group which may have the same or different 1 to 3 groups selected from the following substituent group (C), a C$_{2-6}$ alkenyl group which may have the same or different 1 to 3 groups selected from the following substituent group (C), a C$_{2-6}$ alkynyl group which may have the same or different 1 to 3 groups selected from the following substituent group (C), a C$_{3-8}$ cycloalkyl group which may have the same or different 1 to 3 groups selected from the following substituent group (C), a C$_{6-10}$ aryl group which may have the same or different 1 to 3 groups selected from the following substituent group (D), a C$_{2-9}$ heterocycloalkyl group which may have the same or different 1 to 3 groups selected from the following substituent group (C), or a C$_{1-9}$ heteroaryl group which may have the same or different 1 to 3 groups selected from the following substituent group (D);
G$^2$ represents a hydrogen atom, a C$_{1-6}$ alkyl group which may have the same or different 1 to 3 groups selected from the following substituent group (C), a C$_{2-6}$ alkenyl group which may have the same or different 1 to 3 groups selected from the following substituent group (C), a C$_{2-6}$ alkynyl group which may have the same or different 1 to 3 groups selected from the following substituent group (C), a C$_{3-8}$ cycloalkyl group which may have the same or different 1 to 3 groups selected from the following substituent group (C), a C$_{6-10}$ aryl group which may have the same or different 1 to 3 groups selected from the following substituent group (D), a C$_{2-9}$ heterocycloalkyl group which may have the same or different 1 to 3 groups selected from the following substituent group (C), or a C$_{1-9}$ heteroaryl group which may have the same or different 1 to 3 groups selected from the following substituent group (D), and with the proviso that G$^2$ may be the same or different when there are 2 or more G$^2$ in the substituents;

G³ represents a $C_{1-6}$ alkyl group;

G⁴ represents a $C_{1-6}$ alkyl group which may have the same or different 1 to 3 groups selected from the following substituent group (C), and with the proviso that G⁴ may be the same or different when there are 2 or more G⁴ in the substituents;

[Substituent Group (C)]:

a halogen atom, a nitro group, a cyano group, an oxo group, -G⁵, —OG⁶, —SG⁶, —N(G⁶)₂, —C(=O)G⁶, —C(=O)OG⁶, —C(=O)N(G⁶)₂, —S(=O)₂G⁶, —S(=O)₂OG⁶, —S(=O)₂N(G⁶)₂, —S(=O)G⁵, —OC(=O)G⁵, —OC(=O)N(G⁶)₂, —NHC(=O)G⁶, —OS(=O)₂G⁵, —NHS(=O)₂G⁵ and —C(=O)NHS (=O)₂G⁵; and

[Substituent Group (D)]:

a halogen atom, a nitro group, a cyano group, -G⁵, —OG⁶, —SG⁶, —N(G⁶)₂, —C(=O)G⁶, —C(=O)OG⁶, —C(=O)N(G⁶)₂, —S(=O)₂G⁶, —S(=O)₂OG⁶, —S(=O)₂N(G⁶)₂, —S(=O)G⁵, —OC(=O)G⁵, —OC (=O)N(G⁶)₂, —NHC(=O)G⁶, —OS(=O)₂G⁵, —NHS(=O)₂G⁵ and —C(=O)NHS(=O)₂G⁵;

in the substituent group (C) and/or (D),

G⁵ represents a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group; and G⁶ represents a hydrogen atom, a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a $C_{2-9}$ heterocycloalkyl group or a $C_{1-9}$ heteroaryl group, and with the proviso that G⁶ may be the same or different when there are 2 or more G⁶ in the substituents, or a pharmaceutically acceptable salt thereof or a prodrug thereof.

2. A pyrazole derivative as claimed in claim 1, wherein Q represents a group represented by the formula: -Z-Ar¹ wherein Ar¹ represents a $C_{6-10}$ aryl group which may have the same or different 1 to 3 groups selected from the following substituent group (B); and Z represents —O—, —S— or —NY— (in which Y represents a hydrogen atom or a $C_{1-6}$ alkyl group), an aliphatic cyclic amino group which may have the same or different 1 to 3 groups selected from the following substituent group (A), or an aromatic cyclic amino group which may have the same or different 1 to 3 groups selected from the following substituent group (B); T represents a group selected from

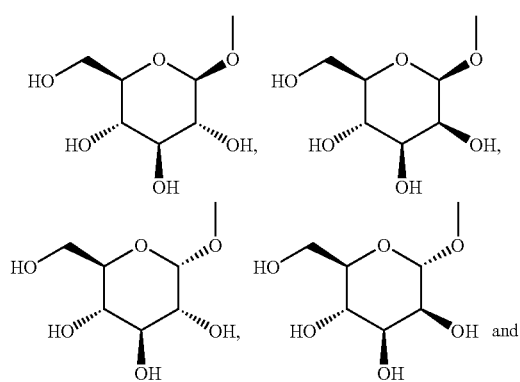

-continued

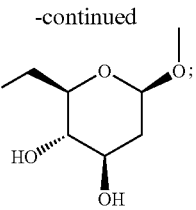

R represents a $C_{6-10}$ aryl group which may have the same or different 1 to 3 groups selected from the following substituent group (B);

[Substituent Group (B)]:

a halogen atom, a nitro group, a cyano group, -G¹, —OG², —SG², —N(G²)₂, -G³OG⁴, -G³N(G⁴)₂, —C(=O)G², —C(=O)OG², —C(=O)N(G²)₂, —S(=O)₂G², —S(=O)₂OG², —S(=O)₂N(G²)₂, —S(=O)G¹, —OC(=O)G¹, —OC(=O)N(G²)₂, —NHC(=O)G², —OS(=O)₂G¹, —NHS(=O)₂G¹ and —C(=O)NHS (=O)₂G¹;

in the above substituent group (B),

G¹ represents a $C_{1-6}$ alkyl group which may have the same or different 1 to 3 groups selected from the following substituent group (C), a $C_{2-6}$ alkenyl group which may have the same or different 1 to 3 groups selected from the following substituent group (C), a $C_{2-6}$ alkynyl group which may have the same or different 1 to 3 groups selected from the following substituent group (C), a $C_{3-8}$ cycloalkyl group which may have the same or different 1 to 3 groups selected from the following substituent group (C), a $C_{6-10}$ aryl group which may have the same or different 1 to 3 groups selected from the following substituent group (D), a $C_{2-9}$ heterocycloalkyl group which may have the same or different 1 to 3 groups selected from the following substituent group (C), or a $C_{1-9}$ heteroaryl group which may have the same or different 1 to 3 groups selected from the following substituent group (D);

G² represents a hydrogen atom, a $C_{1-6}$ alkyl group which may have the same or different 1 to 3 groups selected from the following substituent group (C), a $C_{2-6}$ alkenyl group which may have the same or different 1 to 3 groups selected from the following substituent group (C), a $C_{2-6}$ alkynyl group which may have the same or different 1 to 3 groups selected from the following substituent group (C), a $C_{3-8}$ cycloalkyl group which may have the same or different 1 to 3 groups selected from the following substituent group (C), a $C_{6-10}$ aryl group which may have the same or different 1 to 3 groups selected from the following substituent group (D), a $C_{2-9}$ heterocycloalkyl group which may have the same or different 1 to 3 groups selected from the following substituent group (C), or a $C_{1-9}$ heteroaryl group which may have the same or different 1 to 3 groups selected from the following substituent group (D), and with the proviso that G² may be the same or different when there are 2 or more G² in the substituents;

G³ represents a $C_{1-6}$ alkyl group;

G⁴ represents a $C_{1-6}$ alkyl group which may have the same or different 1 to 3 groups selected from the following substituent group (C), and with the proviso that G⁴ may be the same or different when there are 2 or more G⁴ in the substituents;

[Substituent Group (C)]:
a halogen atom, a nitro group, a cyano group, an oxo group, -G$^5$, —OG$^6$, —SG$^6$, —N(G$^6$)$_2$, —C(=O)G$^6$, —C(=O)OG$^6$, —C(=O)N(G$^6$)$_2$, —S(=O)$_2$G$^6$, —S(=O)$_2$OG$^6$, —S(=O)$_2$N(G$^6$)$_2$, —S(=O)$_2$G$^5$, —OC(=O)G$^5$, —OC(=O)N(G$^6$)$_2$, —NHC(=O)G$^6$, —OS(=O)$_2$G$^5$, —NHS(=O)$_2$G$^5$ and —C(=O)NHS(=O)$_2$G$^5$; and

[Substituent Group (D)]:
a halogen atom, a nitro group, a cyano group, -G$^5$, —OG$^6$, —SG$^6$, —N(G$^6$)$_2$, —C(=O)G$^6$, —C(=O)OG$^6$, —C(=O)N(G$^6$)$_2$, —S(=O)$_2$G$^6$, —S(=O)$_2$OG$^6$, —S(=O)$_2$N(G$^6$)$_2$, —S(=O)$_2$G$^5$, —OC(=O)G$^5$, —OC(=O)N(G$^6$)$_2$, —NHC(=O)G$^6$, —OS(=O)$_2$G$^5$, —NHS(=O)$_2$G$^5$ and —C(=O)NHS(=O)$_2$G$^5$;

in the substituent group (C) and/or (D),
G$^5$ represents a C$_{1-6}$ alkyl group, a C$_{2-6}$ alkenyl group, a C$_{2-6}$ alkynyl, a C$_{3-8}$ cycloalkyl group, a C$_{6-10}$ aryl group, a C$_{2-9}$ heterocycloalkyl group or a C$_{1-9}$ heteroaryl group; and G$^6$ represents a hydrogen atom, a C$_{1-6}$ alkyl group, a C$_{2-6}$ alkenyl group, a C$_{2-6}$ alkynyl, a C$_{3-8}$ cycloalkyl group, a C$_{6-10}$ aryl group, a C$_{2-9}$ heterocycloalkyl group or a C$_{1-9}$ heteroaryl group, and with the proviso that G$^6$ may be the same or different when there are 2 or more G$^6$ in the substituents, or a pharmaceutically acceptable salt thereof or a prodrug thereof.

3. A pharmaceutical composition comprising a pyrazole derivative as claimed in claim 1 or 2, or a pharmaceutically acceptable salt thereof or a prodrug thereof in combination with a pharmaceutical additive.

4. A pharmaceutical composition as claimed in claim 3, wherein the composition is a sodium/glucose cotransporter inhibitor.

5. A pharmaceutical composition as claimed in claim 3, which further comprises at least one drug selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, a hydroxymethylglutaryl coenzyme A reductase inhibitor, a fibric acid derivative, a β$_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an α$_2$-adrenoceptor agonist, an anti-platelets agent, a uric acid synthesis inhibitor, a uricosuric agent and a urinary alkalinizer.

6. A pyrazole derivative represented by the general formula:

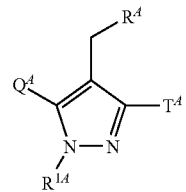

wherein

R$^{1A}$ represents a hydrogen atom, a C$_{1-6}$ alkyl group which may have the same or different 1 to 3 groups selected from the following substituent group (A1), a C$_{2-6}$ alkenyl group which may have the same or different 1 to 3 groups selected from the following substituent group (A1), a C$_{2-6}$ alkynyl group which may have the same or different 1 to 3 groups selected from the following substituent group (A1), a C$_{3-8}$ cycloalkyl group which may have the same or different 1 to 3 groups selected from the following substituent group (A1), a C$_{6-10}$ aryl group which may have the same or different 1 to 3 groups selected from the following substituent group (B1), a C$_{2-9}$ heterocycloalkyl group which may have the same or different 1 to 3 groups selected from the following substituent group (A1), or a C$_{1-9}$ heteroaryl group which may have the same or different 1 to 3 groups selected from the following substituent group (B1);

one of Q$^A$ and T$^A$ represents a group selected from

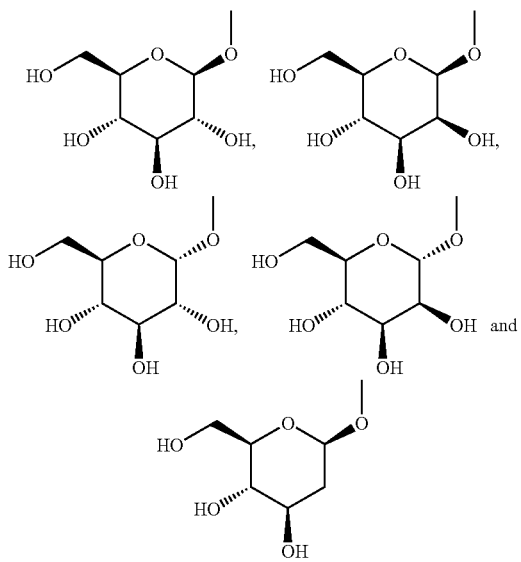

which has a protective group, and the other represents a group represented by the formula: $-Z^A-Ar^A$ wherein $Ar^A$ represents a $C_{6-10}$ aryl group which may have the same or different 1 to 3 groups selected from the following substituent group (B1) or a $C_{1-9}$ heteroaryl group which may have the same or different 1 to 3 groups selected from the following substituent group (B1); and $Z^A$ represents —O—, —S— or —$NY^A$— (in which $Y^A$ represents a hydrogen atom, a $C_{1-6}$ alkyl group or a protective group), an aliphatic cyclic amino group which may have the same or different 1 to 3 groups selected from the following substituent group (A1), or an aromatic cyclic amino group which may have the same or different 1 to 3 groups selected from the following substituent group (B1);

$R^A$ represents a $C_{3-8}$ cycloalkyl group which may have the same or different 1 to 3 groups selected from the following substituent group (A1), a $C_{6-10}$ aryl group which may have the same or different 1 to 3 groups selected from the following substituent group (B1), a $C_{2-9}$ heterocycloalkyl group which may have the same or different 1 to 3 groups selected from the following substituent group (A1), or a $C_{1-9}$ heteroaryl group which may have the same or different 1 to 3 groups selected from the following substituent group (B1);

[Substituent Group (A1)]:

a halogen atom, a nitro group, a cyano group, an oxo group, -$G^{1A}$, —$OG^{2B}$, —$SG^{2B}$, —$N(G^{2B})_2$, —$C(=O)G^{2A}$, —$C(=O)OG^{2B}$, —$C(=O)N(G^{2B})_2$, —$S(=O)_2G^{2A}$, $S(=O)_2OG^{2A}$, —$S(O)_2N(G^{2B})_2$, —$S(=O)G^{1A}$, —OC$(=O)G^{1A}$, —$OC(=O)N(G^{2B})_2$, —$NHC(=O)G^{2A}$, —$OS(O)_2G^{1A}$, —$NHS(=O)_2G^{1A}$ and —$C(=O)NHS(=O)_2G^{1A}$;

[Substituent Group (B1)]:

a halogen atom, a nitro group, a cyano group, -$G^{1A}$, —$OG^{2B}$, $SG^{2B}$, —$N(G^{2B})_2$, -$G^3OG^{4A}$, -$G^3N(G^{4A})_2$, —$C(=O)G^{2A}$, —$C(=O)OG^{2B}$, —$C(=O)N(G^{2B})_2$, —$S(=O)_2G^{2A}$, —$S(=O)_2OG^{2A}$, —$S(=O)_2N(G^{2B})_2$, —$S(=O)_2G^{1A}$, —$OC(=O)G^{1A}$, —$OC(=O)N(G^{2B})_2$, —$NHC(=O)G^{2A}$, —$OS(=O)_2G^{1A}$, $NHS(=O)_2G^{1A}$ and —$C(=O)NHS(=O)_2G^{1A}$;

in the above substituent group (A1) and/or (B1), $G^{1A}$ represents a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1);

$G^{2A}$ represents a hydrogen atom, a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1);

$G^{2B}$ represents a protective group, a hydrogen atom, a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1); and with the proviso that $G^{2B}$ may be the same or different when there are 2 or more $G^{2B}$ in the substituents;

$G^3$ represents a $C_{1-6}$ alkyl group;

$G^{4A}$ represents a $C_{1-6}$ alkyl group which may have the same or different 1 to 3 groups selected from the following substituent group (C1), and with the proviso that $G^{4A}$ may be the same or different when there are 2 or more $G^{4A}$ in the substituents;

[Substituent Group (C1)]:

a halogen atom, a nitro group, a cyano group, an oxo group, -$G^5$, —$OG^{6A}$, —$SG^{6A}$, —$N(G^{6A})_2$, —$C(=O)G^6$, —$C(=O)OG^{6A}$, —$C(=O)N(G^{6A})_2$, —$S(=O)_2G^6$, —$S(=O)_2OG^6$, —$S(=O)_2N(G^{6A})_2$, —$S(=O)G^5$, —$OC(=O)G^5$, —$OC(=O)N(G^{6A})_2$, —$NHC(=O)G^6$, —$OS(=O)_2G^5$, —$NHS(=O)_2G^5$ and —$C(=O)NHS(=O)_2G^5$; and

[Substituent Group (D1)]:

a halogen atom, a nitro group, a cyano group, -$G^5$, $OG^{6A}$, —$SG^{6A}$, —$N(G^{6A})_2$, —$C(=O)G^6$, —$C(=O)OG^{6A}$, —$C(=O)N(G^{6A})_2$, —$S(=O)_2G^6$, —$S(=O)_2OG^6$, —$S(=O)_2N(G^{6A})_2$, —$S(=O)G^5$, —$OC(=O)G^5$, —$OC(=O)N(G^{6A})_2$, —$NHC(=O)G^6$, —$OS(=O)_2G^5$, —$NHS(=O)_2G^5$ and —$C(=O)NHS(=O)_2G^5$;

in the substituent group (C1) and/or (D1), $G^5$ represents a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group; and $G^6$ represents a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group;

$G^{6A}$ represents a protective group, a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group, and with the proviso that $G^{6A}$ may be the same or different when there are 2 or more $G^{6A}$ in the substituents, or a pharmaceutically acceptable salt thereof.

7. A pyrazole derivative represented by the general formula:

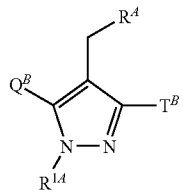

wherein
R$^{1A}$ represents a hydrogen atom, a C$_{1-6}$ alkyl group which may have the same or different 1 to 3 groups selected from the following substituent group (A1), a C$_{2-6}$ alkenyl group which may have the same or different 1 to 3 groups selected from the following substituent group (A1), a C$_{2-6}$ alkynyl group which may have the same or different 1 to 3 groups selected from the following substituent group (A1), a C$_{3-8}$ cycloalkyl group which may have the same or different 1 to 3 groups selected from the following substituent group (A1), a C$_{6-10}$ aryl group which may have the same or different 1 to 3 groups selected from the following substituent group (B1), a C$_{2-9}$ heterocycloalkyl group which may have the same or different 1 to 3 groups selected from the following substituent group (A1), or a C$_{1-9}$ heteroaryl group which may have the same or different 1 to 3 groups selected from the following substituent group (B1);

one of Q$^B$ and T$^B$ represents a hydroxy group, and the other represents a group represented by the formula: -Z$^A$-Ar$^A$ wherein Ar$^A$ represents a C$_{6-10}$ aryl group which may have the same or different 1 to 3 groups selected from the following substituent group (B1) or a C$_{1-9}$ heteroaryl group which may have the same or different 1 to 3 groups selected from the following substituent group (B1); and Z$^A$ represents —O—, —S— or —NY$^A$— (in which Y$^A$ represents a hydrogen atom, a C$_{1-6}$ alkyl group or a protective group), an aliphatic cyclic amino group which may have the same or different 1 to 3 groups selected from the following substituent group (A1), or an aromatic cyclic amino group which may have the same or different 1 to 3 groups selected from the following substituent group (B1);

R$^A$ represents a C$_{3-8}$ cycloalkyl group which may have the same or different 1 to 3 groups selected from the following substituent group (A1), a C$_{6-10}$ aryl group which may have the same or different 1 to 3 groups selected from the following substituent group (B1), a C$_{2-9}$ heterocycloalkyl group which may have the same or different 1 to 3 groups selected from the following substituent group (A1), or a C$_{1-9}$ heteroaryl group which may have the same or different 1 to 3 groups selected from the following substituent group (B1);

[Substituent Group (A1)]:
a halogen atom, a nitro group, a cyano group, an oxo group, -G$^{1A}$, —OG$^{2B}$, —SG$^{2B}$, —N(G$^{2B}$)$_2$, —C(=O)G$^{2A}$, —C(=O)OG$^{2B}$, —C(=O)N(G$^{2B}$)$_2$, —S(=O)$_2$G$^{2A}$, —S(=O)$_2$OG$^{2A}$, —S(=O)$_2$N(G$^{2B}$)$_2$, —S(=O)G$^{1A}$, —OC(=O)G$^{1A}$, —OC(=O)N(G$^{2B}$)$_2$, —NHC(=O)G$^{2A}$, —OS(=O)$_2$G$^{1A}$, —NHS(=O)$_2$G$^{1A}$ and —C(=O)NHS(=O)$_2$G$^{1A}$;

[Substituent Group (B1)]:
a halogen atom, a nitro group, a cyano group, -G$^{1A}$, —OG$^{2B}$, —SG$^{2B}$, —N(G$^{2B}$)$_2$, -G$^3$OG$^{4A}$, -G$^3$N(G$^{4A}$)$_2$, —C(=O)G$^{2A}$, —C(=O)OG$^{2B}$, —C(=O)N(G$^{2B}$)$_2$, —S(=O)$_2$G$^{2A}$, —S(=O)$_2$OG$^{2A}$, —S(=O)$_2$N(G$^{2B}$)$_2$, —S(=O)G$^{1A}$, —OC(=O)G$^{1A}$, —OC(=O)N(G$^{2B}$)$_2$, —NHC(=O)G$^{2A}$, —OS(=O)$_2$G$^{1A}$, —NHS(=O)$_2$G$^{1A}$ and —C(=O)NHS(=O)$_2$G$^{1A}$;

in the above substituent group (A1) and/or (B1),
G$^{1A}$ represents a C$_{1-6}$ alkyl group which may have the same or different 1 to 3 groups selected from the following substituent group (C1), a C$_{2-6}$ alkenyl group which may have the same or different 1 to 3 groups selected from the following substituent group (C1), a C$_{2-6}$ alkynyl group which may have the same or different 1 to 3 groups selected from the following substituent group (C1), a C$_{3-8}$ cycloalkyl group which may have the same or different 1 to 3 groups selected from the following substituent group (C1), a C$_{6-10}$ aryl group which may have the same or different 1 to 3 groups selected from the following substituent group (D1), a C$_{2-9}$ heterocycloalkyl group which may have the same or different 1 to 3 groups selected from the following substituent group (C1), or a C$_{1-9}$ heteroaryl group which may have the same or different 1 to 3 groups selected from the following substituent group (D1);

G$^{2A}$ represents a hydrogen atom, a C$_{1-6}$ alkyl group which may have the same or different 1 to 3 groups selected from the following substituent group (C1), a C$_{2-6}$ alkenyl group which may have the same or different 1 to 3 groups selected from the following substituent group (C1), a C$_{2-6}$ alkynyl group which may have the same or different 1 to 3 groups selected from the following substituent group (C1), a C$_{3-8}$ cycloalkyl group which may have the same or different 1 to 3 groups selected from the following substituent group (C1), a C$_{6-10}$ aryl group which may have the same or different 1 to 3 groups selected from the following substituent group (D1), a C$_{2-9}$ heterocycloalkyl group which may have the same or different 1 to 3 groups selected from the following substituent group (C1), or a C$_{1-9}$ heteroaryl group which may have the same or different 1 to 3 groups selected from the following substituent group (D1);

G$^{2B}$ represents a protective group, a hydrogen atom, a C$_{1-6}$ alkyl group which may have the same or different 1 to 3 groups selected from the following substituent group (C1), a C$_{2-6}$ alkenyl group which may have the same or different 1 to 3 groups selected from the following substituent group (C1), a C$_{2-6}$ alkynyl group which may have the same or different 1 to 3 groups selected from the following substituent group (C1), a C$_{3-8}$ cycloalkyl group which may have the same or different 1 to 3 groups selected from the following substituent group (C1), a C$_{6-10}$ aryl group which may have the same or different 1 to 3 groups selected from the following substituent group (D1), a C$_{2-9}$ heterocycloalkyl group which may have the same or different 1 to 3 groups selected from the following substituent group (C1), or a C$_{1-9}$ heteroaryl group which may have the same or different 1 to 3 groups selected from the following substituent group (D1); and with the proviso that G$^{2B}$ may be the same or different when there are 2 or more G$^{2B}$ in the substituents;

G$^3$ represents a C$_{1-6}$ alkyl group;

G$^{4A}$ represents a C$_{1-6}$ alkyl group which may have the same or different 1 to 3 groups selected from the following substituent group (C1), and with the proviso that G$^{4A}$ may be the same or different when there are 2 or more G$^{4A}$ in the substituents;

[Substituent Group (C1)]:
a halogen atom, a nitro group, a cyano group, an oxo group, -$G^5$, —$OG^{6A}$, —$SG^{6A}$, —$N(G^{6A})_2$, —$C(=O)G^6$, —$C(=O)OG^{6A}$, —$C(=O)N(G^{6A})_2$, —$S(=O)_2G^6$, —$S(=O)_2OG^6$, $S(=O)_2N(G^{6A})_2$, —$S(=O)G^5$, —$OC(=O)G^5$, —$OC(=O)N(G^{6A})_2$, —$NHC(=O)G^6$, —$OS(=O)_2G^5$, —$NHS(=O)_2G^5$ and —$C(=O)NHS(=O)_2G^5$; and

[Substituent Group (D1)]:
a halogen atom, a nitro group, a cyano group, -$G^5$, —$OG^{6A}$, —$SG^{6A}$, —$N(G^{6A})_2$, —$C(=O)G^6$, —$C(=O)OG^{6A}$, —$C(=O)N(G^{6A})_2$, —$S(=O)_2G^6$, —$S(=O)_2OG^6$, —$S(=O)_2N(G^{6A})_2$, —$S(=O)G^5$, —$OC(=O)G^5$, —$OC(=O)N(G^{6A})_2$, —$NHC(=O)G^6$, —$OS(=O)_2G^5$, —$NHS(=O)_2G^5$ and —$C(=O)NHS(=O)_2G^5$;

in the substituent group (C1) and/or (D1), $G^5$ represents a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group;

$G^6$ represents a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group; and $G^{6A}$ represents a protective group, a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group, and with the proviso that $G^{6A}$ may be the same or different when there are 2 or more $G^{6A}$ in the substituents, or a pharmaceutically acceptable salt thereof.

8. A method for the treatment of a disease caused by excess uptake of at least a kind of carbohydrate selected from glucose, fructose and mannose, which comprises administering to a patient in need thereof an effective amount of a pyrazole derivative as claimed in claim 1 or 2, or a pharmaceutically acceptable salt thereof or a prodrug thereof.

9. A method for the treatment as claimed in claim 8, wherein the disease is selected from a group consisting of diabetes, postprandial hyperglycemia, impaired glucose tolerance, diabetic complications, obesity, hyperinsulinemia, hyperlipidemia, hypercholesterolemia, hypertriglyceridemia, lipid metabolism disorders, artherosclerosis, hypertension, congestive heart failure, edematous state, metabolic acidosis, syndrome X, hyperuricemia, gout and nephritis.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial sequence
<220> FEATURE:
<223> OTHER INFORMATION: synthetic PCR primer

<400> SEQUENCE: 1
tgtcacagtc cccaacacca                                              20

<210> SEQ ID NO 2
<211> LENGTH: 19
<212> TYPE: DNA
<213> ORGANISM: Artificial sequence
<220> FEATURE:
<223> OTHER INFORMATION: synthetic PCR primer

<400> SEQUENCE: 2
ccgaagcatg tggaaagca                                               19

<210> SEQ ID NO 3
<211> LENGTH: 18
<212> TYPE: DNA
<213> ORGANISM: Artificial sequence
<220> FEATURE:
<223> OTHER INFORMATION: synthetic probe

<400> SEQUENCE: 3
tgtcacctcc cacggccc                                                18
```